United States Patent
Kim et al.

[11] Patent Number: 5,663,331
[45] Date of Patent: Sep. 2, 1997

[54] CEPHALOSPORIN COMPOUNDS

[75] Inventors: Kee Won Kim; Jae Hoon Kang, both of Seoul; Cheon Ho Park, Kyungki-do, all of Rep. of Korea

[73] Assignee: Il-Dong Pharm. Co., Ltd., Seoul, Rep. of Korea

[21] Appl. No.: 256,348

[22] PCT Filed: Jan. 16, 1993

[86] PCT No.: PCT/KR93/00005

§ 371 Date: Jan. 24, 1995

§ 102(e) Date: Jan. 24, 1995

[87] PCT Pub. No.: WO93/15084

PCT Pub. Date: Aug. 5, 1993

[30] Foreign Application Priority Data

Jan. 23, 1992 [KR] Rep. of Korea ............. 1992-941

[51] Int. Cl.$^6$ ............................................. P07D 501/36
[52] U.S. Cl. ..................................... 540/227; 540/225
[58] Field of Search ............................. 540/227, 225

[56] References Cited

U.S. PATENT DOCUMENTS 4,785,090 11/1988 Tsuruoka et al. ...................... 540/229

*Primary Examiner*—John M. Ford
*Attorney, Agent, or Firm*—Birch, Stewart, Kolasch & Birch, LLP

[57] ABSTRACT

The present invention relates to new cephalosporin compounds of the formula (I), particularly 3-position of cephem rings thereof substituted with new thione compounds and pharmaceutically acceptable salts thereof, which have broad antibacterial activities against both Gram-positive and Gram-negative bacteria, and the said compounds can be prepared by reacting the compounds of the formula (II) with the new thione compounds of the formula (III).

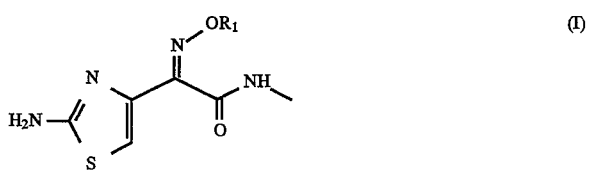

(I)

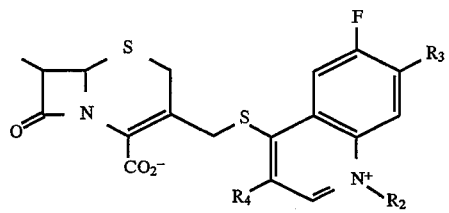

(II)

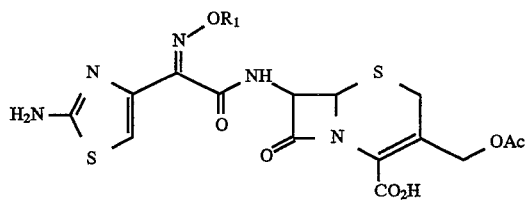

(III)

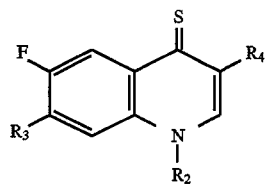

wherein $R_1$ is a $C_{1-4}$ alkyl(preferably methyl or ethyl), $C_{3-4}$ alkenyl(preferably allyl), $C_{3-4}$ alkynyl (preferably propargyl) group or —C($R^a$)($R^b$)CO$_2$H(preferably —C(CH$_3$)$_2$CO$_2$H or —CH$_2$CO$_2$H), wherein $R^1$ and $R^b$, same or different, are a hydrogen atom or a $C_{1-4}$ alkyl group;

$R_2$ is a $C_{1-4}$ alkyl(preferably methyl or ethyl), $C_{3-4}$ alkenyl(preferably allyl), $C_{3-4}$ cycloalkyl(preferably cyclopropyl) group or carboxyalkyl(preferably —CH$_2$CO$_2$H) group;

$R_3$ is a 5- or 6-membered heterocyclic compound-containing 1 or 2 nitrogen atom(s) (preferably piperazine, alkylpiperazine-substituted with $C_{1-4}$ alkyl at N— or 2-position of piperazine, imidazole-substituted or unsubstituted with $C_{1-4}$ alkyl); $R_4$ is hydrogen or a carboxylic acid.

4 Claims, No Drawings

CEPHALOSPORIN COMPOUNDS

This application is a 35 USC §371 of PCT/KR93/0005, filed Jan. 16, 1993.

FIELD OF THE INVENTION

The present invention relates to new cephalosporin compounds of the formula (I), particularly 3-position of cephem rings substituted with new thione compounds and pharmaceutically acceptable salts thereof, which have broad antibacterial activities against both Gram-positive and Gram-negative bacteria.

SUMMARY OF THE INVENTION

An objective of the present invention is to provide new antibiotic cephalosporin compounds of the formula(I) or pharmaceutically acceptable salts thereof

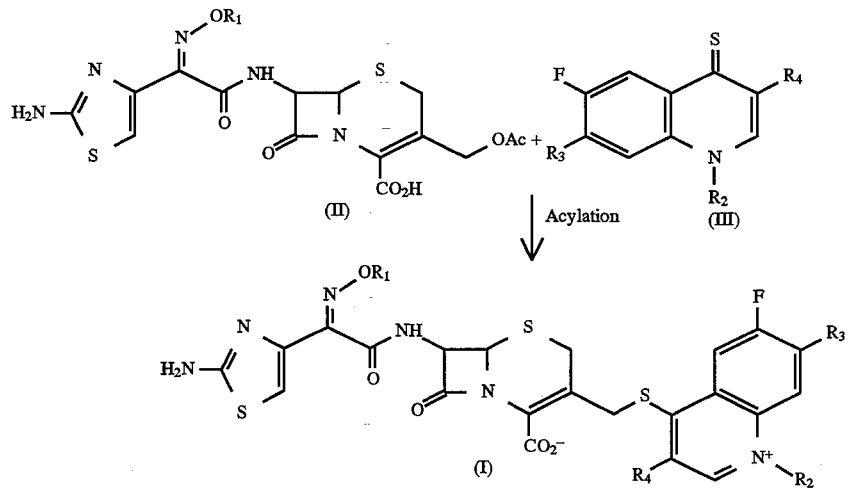

wherein
$R_1$ is a $C_{1-4}$ alkyl (preferably ethyl or ethyl), $C_{3-4}$ alkenyl(preferably allyl), $C_{3-4}$ alkynyl (preferably propargyl) group or —$C(R^a)(R^b)CO_2H$(preferably —$C(CH_3)_2CO_2H$ or —$CH_2CO_2H$), wherein $R^a$ and $R^b$, same or different, are a hydrogen atom or a $C_{1-4}$ alkyl group;

$R_2$ is a $C_{1-4}$ alkyl (preferably methyl or ethyl), $C_{3-4}$ alkenyl (preferably allyl), $C_{3-4}$ cycloalkyl (preferably cyclopropyl)group or carboxyalkyl (preferably —$CH_2CO_2H$)group;

$R_3$ is a 5- or 6-membered heterocyclic compounds-containing 1 or 2 nitrogen atom(s) (preferably piperazine, alkylpiperazine-substituted with $C_{1-4}$ alkyl at N— or 2-position of piperazine, imidazole-substituted or unsubstituted with $C_{1-4}$ alkyl);

$R_4$ is hydrogen or a carboxylic acid.

DETAILED DESCRIPTION OF THE INVENTION

The compounds of the formula(I) can be prepared by reacting the compounds of the formular(II) with the new thione compounds of the formular (III), as follows:

wherein
$R_1$ is a methyl, allyl, propargyl group or —$C(CH_3)_2CO_2H$;

$R_2, R_3$ and $R_4$ are the same as defined above.

In the preparation of the objective compounds(I), the compounds of the formula(III) are used preferably in an amount of from 1 to 2 equivalent(s) based on 1 equivalent of the compounds of the formula(II). The reaction for introducing the compounds(III) into the 3-position of compound(II) to prepare compounds(I) is carried out in the presence of a solvent such as water, N,N-dimethylformamide, dimethylsulfoxide, or a mixed agueous solvent of water. An appropriate water-miscible solvent is acetonitrile or acetone.

Also, the reaction may be carried out at 40° C. to 100° C., preferably 60° C. to 80° C.

To stabilize reaction products and their intermediates, one or more salts selected from the group consisting of sodium iodide and potassium iodide can be used as stabilizing agents.

On the other hand, the separation and purification of the compounds(I) can be carried out using a known method such as recrystallization, column chromatography over silica gel or ion-exchange chromatography.

The new thione compounds of the formula(III) can be prepared from quinolone compounds which prepared by known method, as follows:

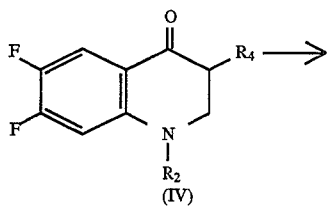
(IV)

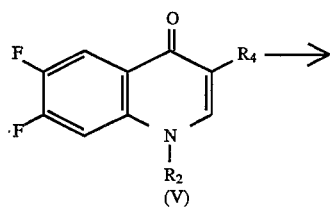
(V)

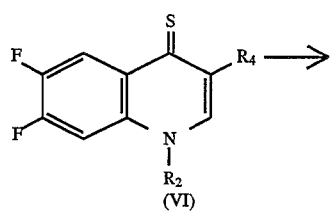
(VI)

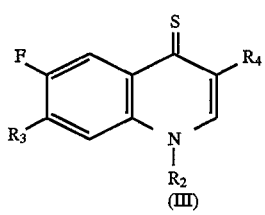
(III)

wherein $R_2$ is a methyl cyclopropyl, ethyl or allyl group;

$R_4$ is hydrogen;

$R_3$ is the same as defined above.

The compounds of the formula(IV) can be prepared by reacting quinolone compounds, sodium borohydride with p-toluenesulfonic acid in the polar solvent, preferably alcohol.

The compounds of the formula(V) can be prepared by reacting the compounds of the formular(IV) with p-chloranil in the polar solvent, preferably 1,4-dioxane at 50° C. to 100° C.

Also, the compounds of the formula(VI) can be prepared by reacting the compounds of the formular(V) with phosphorus pentasulfide in the polar solvent, preferably acetonitrile, and the new thione compounds of the formula (III) can be prepared by substitution of 5- or 6-membered heterocyclic compounds-containing 1 or 2 nitrogen atom(s) (preferably piperazine, alkylpiperazine-substituted with $C_{1-4}$ alkyl at N— or 2-position of piperazine, imidazole-substituted or unsubstituted with $C_{1-4}$ alkyl) at the 7-position of compounds(VI).

In case $R_4$ is a carboxylic acid, the compounds of the formula(III) can be prepared from the compounds of the formula(VII) which prepared by known method, as follows:

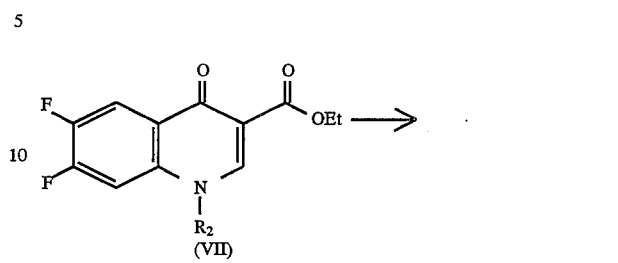
(VII)

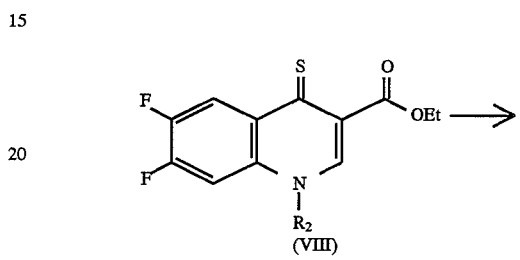
(VIII)

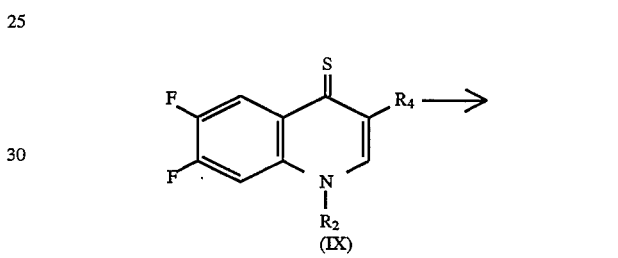
(IX)

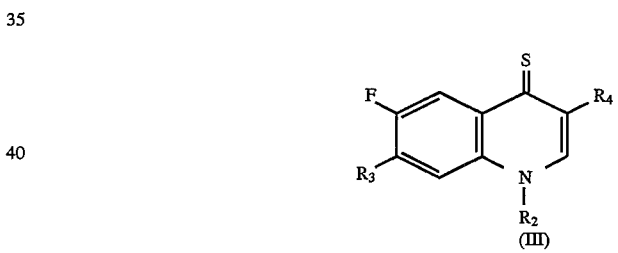
(III)

wherein $R_2$ is a cyclopropyl;

$R_4$ is a carboxylic acid;

$R_3$ is the same as defined above.

The compounds of the formula(VIII) can be prepared by reacting with the compounds of the formular(VII) and phosphorus pentasulfide in the polar solvent, preferably acetonitrile.

The compounds of the formula(IX) can be prepared by hydrolysis of the compounds(VIII).

Also, the compounds of the formula(III) can be prepared by substitution of 5-or 6-membered heterocyclic compounds-containing 1 or 2 nitrogen atom(s) (preferably piperazine, alkylpiperazine-substituted with $C_{1-4}$ alkyl at N— or 2-position of piperazine, imidazole-substituted or unsubstituted with $C_{1-4}$ alkyl) at the 7-position of compounds(IX).

The new thione compounds of the formula(III) are shown in Table 1.

TABLE 1

New Thione Compounds

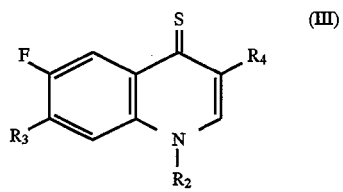

| Compound No. | R₂ | R₃ | R₄ |
|---|---|---|---|
| III-1 | Methyl | Piperazine | H |
| III-2 | Methyl | N-Methylpiperazine | H |
| III-3 | Methyl | 1-Ethylpiperazine | H |
| III-4 | Methyl | 2-Methylpiperazine | H |
| III-5 | Methyl | Imidazole | H |
| III-6 | Methyl | 4-Methylimidazole | H |
| III-7 | Cyclopropyl | Piperazine | H |
| III-8 | Cyclopropyl | N-Methylpiperazine | H |
| III-9 | Cyclopropyl | 1-Ethylpiperazine | H |
| III-10 | Cyclopropyl | 2-Methylpiperazine | H |
| III-11 | Cyclopropyl | Imidazole | H |
| III-12 | Cyclopropyl | 4-Methylimidazole | H |
| III-13 | Cyclopropyl | 1-Ethylpiperazine | COOH |
| III-14 | Cyclopropyl | 2-Methylpiperazine | COOH |
| III-15 | Ethyl | Piperazine | H |
| III-16 | Ethyl | N-Methylpiperazine | H |

TABLE 1-continued

New Thione Compounds

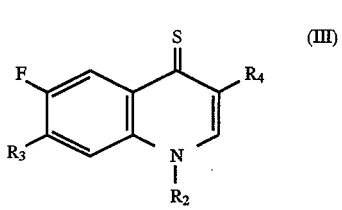

| Compound No. | R₂ | R₃ | R₄ |
|---|---|---|---|
| III-16 | Ethyl | N-Methylpiperazine | H |
| III-17 | Ethyl | 1-Ethylpiperazine | H |
| III-18 | Ethyl | 2-Methylpiperazine | H |
| III-19 | Allyl | Piperazine | H |
| III-20 | Allyl | N-Methylpiperazine | H |
| III-21 | Allyl | 1-Ethylpiperazine | H |
| III-22 | Allyl | 2-Methylpiperazine | H |

The new cephalosporin compounds of the formula(I) are shown in Table 2.

TABLE 2

New Cephalosporin Compounds

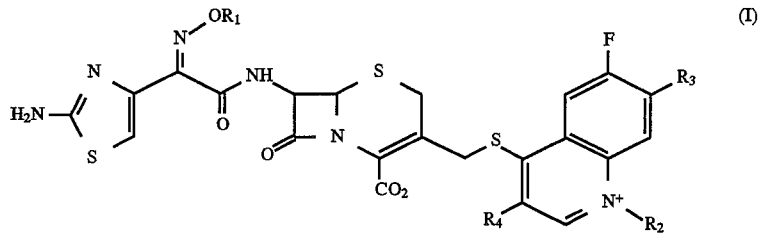

| Compound No. | R₁ | R₂ | R₃ | R₄ |
|---|---|---|---|---|
| I-1 | CH₃ | Methyl | Piperazine | H |
| I-2 | CH₃ | Methyl | N-Methylpiperazine | H |
| I-3 | CH₃ | Methyl | 1-Ethylpiperazine | H |
| I-4 | CH₃ | Methyl | 2-Methylpiperazine | H |
| I-5 | CH₃ | Cyclopropyl | Piperazine | H |
| I-6 | CH₃ | Cyclopropyl | N-Methylpiperazine | H |
| I-7 | CH₃ | Cyclopropyl | 1-Ethylpiperazine | H |
| I-8 | CH₃ | Cyclopropyl | 2-Methylpiperazine | H |
| I-9 | CH₃ | Ethyl | Piperazine | H |
| I-10 | CH₃ | Ethyl | N-Methylpiperazine | H |
| I-11 | CH₃ | Ethyl | 1-Ethylpiperazine | H |
| I-12 | CH₃ | Ethyl | 2-Methylpiperazine | H |
| I-13 | CH₃ | Allyl | Piperazine | H |
| I-14 | CH₃ | Allyl | N-Methylpiperazine | H |
| I-15 | CH₃ | Allyl | 1-Ethylpiperazine | H |
| I-16 | CH₃ | Allyl | 2-Methylpiperazine | H |
| I-17 | CH₃ | Methyl | Imidazole | H |
| I-18 | CH₃ | Methyl | 4-Methylimidazole | H |
| I-19 | CH₃ | Cyclopropyl | Imidazole | H |
| I-20 | CH₃ | Cyclopropyl | 4-Methylimidazole | H |
| I-21 | —CH₂CHCH₂ | Methyl | Piperazine | H |
| I-22 | —CH₂CHCH₂ | Methyl | N-Methylpiperazine | H |
| I-23 | —CH₂CHCH₂ | Methyl | 1-Ethylpiperazine | H |
| I-24 | —CH₂CHCH₂ | Methyl | 2-Methylpiperazine | H |
| I-25 | —CH₂CHCH₂ | Cyclopropyl | Piperazine | H |
| I-26 | —CH₂CHCH₂ | Cyclopropyl | N-Methylpiperizine | H |

TABLE 2-continued

New Cephalosporin Compounds

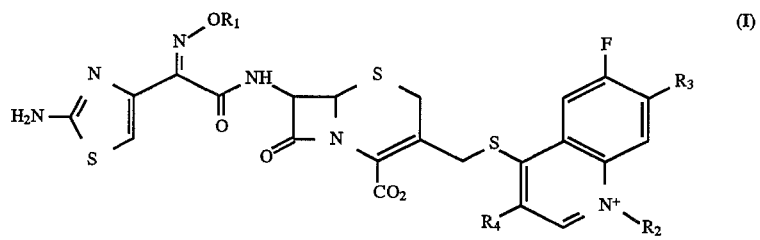

| Compound No. | $R_1$ | $R_2$ | $R_3$ | $R_4$ |
|---|---|---|---|---|
| I-27 | —$CH_2CHCH_2$ | Cyclopropyl | 1-Ethylpiperazine | H |
| I-28 | —$CH_2CHCH_2$ | Cyclopropyl | 2-Methylpiperazine | H |
| I-29 | —$CH_2CHCH_2$ | Ethyl | Piperazine | H |
| I-30 | —$CH_2CHCH_2$ | Ethyl | N-Methylpiperazine | H |
| I-31 | —$CH_2CHCH_2$ | Ethyl | 1-Ethylpiperazine | H |
| I-32 | —$CH_2CHCH_2$ | Ethyl | 2-Methylpiperazine | H |
| I-33 | —$CH_2CHCH_2$ | Allyl | Piperazine | H |
| I-34 | —$CH_2CHCH_2$ | Allyl | N-Methylpiperazine | H |
| I-35 | —$CH_2CHCH_2$ | Allyl | 1-Ethylpiperazine | H |
| I-36 | —$CH_2CHCH_2$ | Allyl | 2-Methylpiperazine | H |
| I-37 | —$CH_2CCH$ | Methyl | Piperazine | H |
| I-38 | —$CH_2CCH$ | Methyl | N-Methylpiperazine | H |
| I-39 | —$CH_2CCH$ | Methyl | 1-Ethylpiperazine | H |
| I-40 | —$CH_2CCH$ | Methyl | 2-Methylpiperazine | H |
| I-41 | —$CH_2CCH$ | Cyclopropyl | Piperazine | H |
| I-42 | —$CH_2CCH$ | Cyclopropyl | N-Methylpiperazine | H |
| I-43 | —$CH_2CCH$ | Cyclopropyl | 1-Ethylpiperazine | H |
| I-44 | —$CH_2CCH$ | Cyclopropyl | 2-Methylpiperazine | H |
| I-45 | —$CH_2CCH$ | Ethyl | Piperazine | H |
| I-46 | —$CH_2CCH$ | Ethyl | N-Methylpiperazine | H |
| I-47 | —$CH_2CCH$ | Ethyl | 1-Ethylpiperazine | H |
| I-48 | —$CH_2CCH$ | Ethyl | 2-Methylpiperazine | H |
| I-49 | —$CH_2CCH$ | Allyl | Piperazine | H |
| I-50 | —$CH_2CCH$ | Allyl | N-Methylpiperazine | H |
| I-51 | —$CH_2CCH$ | Allyl | 1-Ethylpiperazine | H |
| I-52 | —$CH_2CCH$ | Allyl | 2-Methylpiperazine | H |
| I-53 | —$C(CH_3)_2CO_2H$ | Methyl | Piperazine | H |
| I-54 | —$C(CH_3)_2CO_2H$ | Methyl | N-Methylpiperazine | H |
| I-55 | —$C(CH_3)_2CO_2H$ | Methyl | 1-Ethylpiperazine | H |
| I-56 | —$C(CH_3)_2CO_2H$ | Methyl | 2-Methylpiperazine | H |
| I-57 | —$C(CH_3)_2CO_2H$ | Cyclopropyl | Piperazine | H |
| I-58 | —$C(CH_3)_2CO_2H$ | Cyclopropyl | N-Methylpiperazine | H |
| I-59 | —$C(CH_3)_2CO_2H$ | Cyclopropyl | 1-Ethylpiperazine | H |
| I-60 | —$C(CH_3)_2CO_2H$ | Cyclopropyl | 2-Methylpiperazine | H |
| I-61 | —$C(CH_3)_2CO_2H$ | Ethyl | 1-Ethylpiperazine | H |
| I-62 | —$C(CH_3)_2CO_2H$ | Ethyl | 2-Methylpiperazine | H |
| I-63 | —$C(CH_3)_2CO_2H$ | Allyl | 1-Ethylpiperazine | H |
| I-64 | —$C(CH_3)_2CO_2H$ | Allyl | 2-Methylpiperazine | H |
| I-65 | —$C(CH_3)_2CO_2H$ | Methyl | Imidazole | H |
| I-66 | —$C(CH_3)_2CO_2H$ | Methyl | 4-Methylimidazole | H |
| I-67 | —$C(CH_3)_2CO_2H$ | Cyclopropyl | Imidazole | H |
| I-68 | —$C(CH_3)_2CO_2H$ | Cyclopropyl | 4-Methylimidazole | H |
| I-69 | $CH_3$ | Cyclopropyl | 1-Ethylpiperazine | $CO_2H$ |
| I-70 | $CH_3$ | Cyclopropyl | 2-Methylpiperazine | $CO_2H$ |
| I-71 | —$C(CH_3)_2CO_2H$ | Cyclopropyl | 1-Ethylpiperazine | $CO_2H$ |
| I-72 | —$C(CH_3)_2CO_2H$ | Cyclopropyl | 2-Methylpiperazine | $CO_2H$ |

The present invention is described in detail by the following Preparations and Examples:

Preparation 1

Preparation of 1-methyl-6,7-difluoro-1,4-dihydro-4-thioquinoline

A. Preparation of 1-methyl-6,7-difluro-1,2,3,4-tetrahydro-4-oxoquinoline

1-Methyl-6,7-difluoro-1,4-dihydro-4-oxoquinoline carboxylic acid(7 g) was added to methyl alcohol(800 ml), and stirred at 0° C. After sodium borohydride(4.3 g) and p-toluene sulfonic acid(cat.amount) were added thereto, the reaction mixture was refuluxed for an hour, and the organic solvent was removed under reduced pressure. To the residue was added chloroform(500 ml), and it was washed twice with water (200 ml). The separated organic layer was dehydrated, and concentrated. The residue was solidified with pet. ether, and dried to give the bright-yellow-above-indicated compound(3.6 g).

m.p.: 65°–67.5° C.

Yield: 77%

NMR: δ($CDCl_3$) 2.65(t,2H), 2.90(s,3H), 3.40(t,2H), 6.40 (dd,1H), 7.78(m,1H)

B. Preparation of 1-methyl-6,7-difluoro-1,4-dihydro-4-oxoquinoline

1-Methyl-6,7-difluoro-1,2,3,4-tetrahydro-4-oxoquinoline (3.19 g) was added to 1,4-dioxane(90 ml). After p-chloranil (7.5 g) was added thereto, the reaction mixture was stirred at 80° C. After 24 hours, the organic solvent was removed under reduced pressure. To the residue was added chloroform(100 ml), and it was washed with 1N-sodium hydroxide solution and water. The separated organic layer was dehydrated, and concentrated. The residue was solidified with pentane, and dried to give the white above-indicated compound(1.6 g).

m.p.: 173.5°–175.5° C.

Yield: 52%

NMR: δ(CDCl$_3$) 3.75(s,3H), 6.20(d,1H), 7.20(ad,1H), 7.50(d,1H), 8.20(dd,1H)

C. Preparation of 1-methyl-6,7-difluoro-1,4-dihydro-4-thioquinoline

1-Methyl-6,7-difluoro-1,4-dihydro-4-oxoquinoline(1.6 g), phosphorus pentasulfide (5.3 g), and sodium bicarbonate (4.0 g) were added to acetonitrile(50 ml), and stirred at 60° C. for 4 hours, cooled to room temperature. The precipitates were filtered, and dried to give the yellow above-indicated compound(1.36 g).

m.p.: 198°–200° C.

Yield: 77%

NMR: δ(CDCl$_3$) 3.90(s,3H), 7.30(d,1H), 7.55–7.85(m, 2H), 8.50–8.85(dd,1H)

Preparation 2

Preparation of 1-cyclopropyl-6,7-difluoro-1,4-dihydro-4-thioquinoline

A. Preparation of 1-cyclopropyl-6,7-difluoro-1,2,3,4-tetrahydro-4-oxoquinoline 1-Cyclopropyl-6,7-difluoro-1,4-dihydro-4-oxoquinoline carboxylic acid(20 g) and sodium borohydride(11.5 g) were reacted in the same method as described in Preparation 1-A to give the yellow above-indicated compound(12 g).

m.p.: 77.8°–80.4° C.

Yield: 86%

NMR: δ(CDCl$_3$) 0.65–1.05(m,4H), 2.20–2.40(m,1H), 2.60(t,2H), 3.50(t,2H), 7.05(dd,1H), 7.70(dd,1H)

B. Preparation of 1-cyclopropyl-6,7-difluoro-1,4-dihydro-4-oxoquinoline

1-Cyclopropyl-6,7-difluoro-1,2,3,4-tetrahydro-4-oxoquinoline(10 g) and p-chloranil (22 g) were reacted in the same method as described in Preparation 1-B to give the white above-indicated compound(8.6 g).

m.p.: 169.6°–172° C.

Yield: 87%

NMR: δ(CDCl$_3$) 0.95–1.40(m,4H), 3.20–3.45(m,1H), 6.15(d,1H), 7.50–7.80(m,2H), 8.10(dd,1H)

C. Preparation of 1-cyclopropyl-6,7-difluoro-1,4-dihydro-4-thioquinoline

1-Cyclopropyl-6,7-difluoro-1,4-dihydro-4-oxoquinoline(4.8 g) and phosphorus pentasulfide(14.6 g) were reacted in the same method as described in preparation 1-C to give the yellow above-indicated compound(4.98).

m.p.: 178°–177° C.

Yield: 94%

NMR: δ(CDCl$_3$) 0.90–1.45(m,4H), 3.25–3.60(m,1H), 7.20–7.50(m,2), 7.60–7.92(dd,1H), 8.55–8.85(dd,1H)

Preparation 3:

Preparation of 1-ethyl,-6,7-difluoro-1,4-dihydro-4-thioquinoline

A. Preparation of 1-ethyl-6,7-difluoro-1,2,3,4-tetrahydro-4-oxoquinoline

1-Ethyl-6,7-difluoro-1,4-dihydro-4-oxoquinoline carboxylic acid(20 g) and sodium borohydride(12 g) were reacted in the same method as described in Preparation 1-A to give the bright-yellow above-indicated compound(11 g).

m.p.: 82°–84° C.

Yield: 80%

NMR: δ(CDCl$_3$) 1.15(t,3H), 2.70(t,2H), 3.40(q,2H), 3.50 (t,2H), 6.50(dd,1H), 7.65(dd,1H)

B. Preparation of 1-ethyl-6,7-difluoro-1,4-dihydro-4-oxoquinoline

1-Ethyl-6,7-difluoro-1,2,3,4-tetrahydro-5-oxoquinoline(10 g) and p-chloranil (23 g) were reacted in the same method as described in Preparation 1-B to give the white above-indicated compound(6.7 g).

m.p.: 176°–178° C.

Yield: 68%

NMR: δ(CDCl$_3$) 1.20(t,3H), 4.10(q,2H), 6.20(d,1H), 7.70–8.05(m,2H), 8.20(dd,1H)

C. Preparation of ethyl-6,7-difluoro-1,4-dihydro-4-thioquinoline

1-Ethyl-6,7-difluoro-1,4-dihydro-4-oxoquinoline(6.7 g) and phosphorus pentasulfide(21 g) were reacted in the same method as described in Preparation 1-C to give the yellow above-indicated compound(4.4 g).

m.p.: 174°–176° C.

Yield: 60%

NMR: δ(CDCl$_3$) 1.40(t,3H), 4.40(q,2H), 7.30(d,1H), 7.95 (d,1H), 8.15(dd,1H), 8.65(dd,1H)

Preparation 4:

Preparation of 1-allyl-6,7-difluoro-1,4-dihydro-4-thioquinoline

A. Preparation of 1-allyl-6,7-difluoro-1,2,3,4-tetrahydro-4-oxoquinoline

1-Allyl-6,7-difluoro-1,4-dihydro-4-oxoquiniline carboxylic acid(25 g) and sodium borohydride(14.2 g) were reacted in the same method as described in Preparsation 1-A to give the bright-yellow above-indicated compound(14 g).

m.p.: 57°–59° C.

Yield: 80%

NMR: δ(CDCl$_3$) 2.70(t,2H), 3.55(t,2H), 3.95(d,2H), 5.25 (dd,2H), 5.75–5.90(m,1H), 6.50(dd,1H), 7.65(dd,1H),

B. Preparation of 1-allyl-6,7-difluoro-1,4-dihydro-4-oxoquinoline

1-Allyl-6,7-difluoro-1,2,3,4-tetrahydro-4-oxoquinoline (13.3 g) and p-chloranil (29.3 g) were reacted in the same method as described in Preparation 1-B to give the white above-indicated compound(12.3 g).

m.p.: 172°–174° C.

Yield: 93%

NMR: δ(CDCl$_3$) 4.70(d,2H), 5.18(d,1H), 5.38(d,1H), 5.95–6.10(m,1H), 6.28(d,1H), 7.25(dd,1H), 7.55(d,1H), 8.25(dd,1H)

C. Preparation of 1-allyl-6,7-difluoro-1,4-dihydro-4-thioquinoline

1-Allyl-6,7-difluoro-1,4-dihydro-4-oxoquinoline(12 g) and phosphorus pentasulfide(36 g) were reacted in the same method as described in Preparation 1-C to give the yellow above-indicated compound(10 g).

m.p.: 160°–163° C. (dec.)
Yield: 77%
NMR: δ(CDCl₃) 5.05(d,2H), 5.15(d,1H), 5.25(d,1H), 5.98–6.10(m,1H), 7.35(d,1H), 7.95–8.05(m,2H), 8.65(dd, 1H)

Preparation 5:

Preparation of 1-methyl-6-fluoro-7-piperazinyl-1,4-dihydro-4-thioquinoline

1-Methyl-6,7-difluoro-1,4-dihydro-4-thioquinoline(1.2 g) and piperazine (1.4 g) were added to pyridine(7 ml), and stirred at 130° C. for an hour. The organic solvent was removed under reduced pressure. To the residue was added chloroform(50 ml), and it was washed with water. The separated organic layer was dehydrated, and concentrated. The residue was solidified with water, and dried to give the yellow above-indicated compound(0.9 g).

m.p.: 255° C.
Yield: 54%
NMR: δ(DMSO-d₆) 2.60–3.10(m,8H), 3.90(s,3H), 7.10–7.65(m,3H), 8.40(d,1H)

Preparation 6:

Preparation of 1-methyl-6-fluoro-7-(N-methylpiperazinyl)-1,4-dihydro-4-thioquinoline 1-Methyl-6,7-difluoro-1,4-thioquinoline(1.2 g) and N-methylpiperazine(1.9 ml) were reacted in the same method as described in Preparation 5 to give the yellow above-indicated compound(1.1 g).

m.p.: 226°–228° C.(dec.)
Yield: 63%
NMR: δ(DMSO-d₆) 2.38(s,3H), 2.60(t,4H), 3.30(t,4H), 3.75(s,3H), 6.58(d,1H), 7.05(m,2H), 8.40(d,1H)

Preparation 7:

Preparation of 1-methyl-6-fluoro-7-(1-ethylpiperazinyl)-1,4-dihydro-4-thioquinoline 1-Methyl-6,7-difluoro-1,4-thioquinoline(6 g) and 1-ethylpiparazine(9.5 g) were reacted in the same method as described in Preparation 5 to give the yellow above-indicated compound(4.2 g).

m.p.: 214°–216° C.(dec.)
Yield: 54%
NMR: δ(DMSO-d₆) 1.15(t,3H), 2.30–2.80(m,6H), 3.30(t, 4H), 3.80(s,3H), 6.60(d,1H), 7.05–7.25(m,2H), 8.50(d,1H)

Preparation 8:

Preparation of 1-methyl-6-fluoro-7-(2-methylpiperazinyl)-1,4-dihydro-4-thioquinoline 1-Methyl-6,7-difluoro-1,4-thioquinoline(4.9 g) and 2-methylpiperazine(6.8 g) were reacted in the same method as described in Preparation 5 to give the yellow above-indicated compound(4.0 g).

m.p.: 177°–179° C.
Yield: 56%
NMR: δ(DMSO-d₆) 1.70(s,3H), 2.70–3.30(m,3H), 3.40–3.70(m,4H), 3.90(s,3H), 6.65(d,1H), 7.05–7.30(m, 2H), 8.50(d,1H)

Preparation 9:

Preparation of 1-methyl-6-fluoro-7-imidazolyl-1,4-dihydro-4-thioquinoline

1-Methyl-6,7-difluoro-1,4-thioquinoline(2 g) and imidazole(1.9 g) were added to pyridine(20 ml), and stirred at 130° C. for 5 hours. The organic solvent was removed under reduced pressure. The residue was solidified with water, and dried to give the yellow above-indicated compound(1.3 g).

m.p.: 255°–257° C.(dec.)
Yield: 51%
NMR: δ(DMSO-d₆) 3.90(s,3H), 7.15–7.25(m,2H), 7.70–8.40(m,4H), 8.50(d,1H)

Preparation 10:

Preparation of 1-methyl-6-fluoro-7-(4-methylimidazolyl)-1,4-dihydro-4-thioquinoline 1-Methyl-6,7-difluoro-1,4-thioquinoline(2 g) and 4-methylimidazole(2.3 g) were reacted in the same method as described in Preparation 9 to give the yellow above-indicated compound(1.4 g).

m.p.: 278°–280° C.(dec.)
Yield: 52%
NMR: δ(DMSO-d₆) 2.40(s,3H), 3.90(s,3H), 6.90–8.35 (m,5H), 8.60(d,1H)

Preparation 11:

Preparation of 1-cyclopropyl-6-fluoro-7-piperazinyl-1,4-dihydro-4-thioquinoline

1-Cyclopropyl-6,7-difluoro-1,4-thioquinoline(1.5 g) and piperazine(1.64 g) were reacted in the same method as described in Preparation 9 to give the yellow above-indicated compound(1.1 g).

m.p.: 205°–208.3° C.
Yield: 55%
NMR: δ(DMSO-d₆) 0.90–1.40(m,4H), 2.65–3.60(m,9H), 7.05–7.70(m,3H), 8.40(d,1H)

Preparation 12:

Preparation of 1-cyclopropyl-6-fluoro-7-(N-methylpiperazinyl)-1,4-dihydro-4-thioquinoline 1-Cyclopropyl-6,7-difluoro-1,4-thioquinoline(1.5 g) and N-methylpiperazine (2.1 ml) were reacted in the same method as described in Preparation 9 to give the yellow above-indicated compound(1.1 g).

m.p.: 181.5°–183.7° C.
Yield: 52%
NMR: δ(DMSO-d₆) 0.95–1.40(m,4H),2.38(s,3H), 2.62(t, 4H), 3.30(t,4H). 3.40–3.62(m,1H), 7.00–7.40(m,3H), 8.40 (d,1H).

Preparation 13:

Preparation of 1-cyclopropyl-6-fluoro-7-(1-ethylpiperazinyl)-1,4-dihydro-4-thioquinoline 1-Cyclopropyl-6,7-difluoro-1,4-thioquinoline (5 g) and 1-ethylpiperazine 7.3 g) were reacted in the same method as described in Preparation 9 to give the yellow above-indicated compound(4.0 g).

m.p.: 178°–180° C.
Yield: 54%
NMR: δ(DMSO-d₆) 0.95–1.40(m,4H),2.30–2.75(m,6H), 3.30(t,4H), 3.40–3.60(m,1H), 7.05–7.40(dd,3H), 8.45 (d,1H), Preparation 14:

Preparation of 1-cyclopropyl-6-fluoro-7-(2-methylpiperazinyl)-1,4-dihydro-4-thioquinoline 1-Cyclopropyl6,7-difluoro-1,4-thioquinoline(5 g) and 2-methylpiperazine(6.4 g) were reacted in the same method as described in Preparation 9 to give the yellow above-indicated compound(4.8 g).

m.p.: 132°–132° C.(dec.)

Yield: 89%

NMR: δ(DMSO-d$_6$) 0.90–1.40(m,7H),2.40–3.75(m,8H), 7.10–7.38(dd,3H), 8.50(d,1H)

Preparation 15:

Preparation of 1-cyclopropyl-6-fluoro-7-imidazolyl-1,4-dihydro-4-thioquinoline 1-Cyclopropyl-6,7-difluoro-1,4-thioquinoline(5 g) and imidazole(4.3 g) were reacted in the same method as described in Preparation 9 to give the yellow above-indicated compound(2.8 g).

m.p.: 205°–207° C.(dec.)

Yield: 45%

NMR: δ(DMSO-d$_6$) 1.10–1.20(m,2H), 1.28–1.38(m,2H), 3.65–3.85(m,1H), 7.25(dd,2H), 7.80(s,1H), 7.95(dd,1H), 8.25(dd1H), 8.35(d,1H), 8.55(d,1H)

Preparation 16:

Preparation of 1-cyclopropyl-6-fluoro-7-(4-methylimidazolyl)-1,4-dihydro-4-thioquinoline 1-Cyclopropyl-6,7-difluoro-1,4-thioquinoline(2.5 g) and 4-methylpiperazine(2.6 g) were reacted in the same method as described in Preparation 9 to give the yellow above-indicated compound(1.9 g).

m.p.: 242°–244° C.(dec.)

Yield: 58%

NMR: δ(DMSO-d$_6$) 1.00–1.35(m,4H), 2.45(s,3H), 3.72–3.85(m,1H), 6.90(s,1H), 7.25–8.35(m,4H), 8.60(d,1H)

Preparation 17:

Preparation of 1-cyclopropyl-6-fluoro-7-(1-ethylpiperazinyl)-1,4-dihydro-4-thioquinoline-3-carboxylic acid 1-Cyclopropyl-6,7-difluoro-1,4-thioquinoline-3-carboxylic acide(1.8 g) and 1-ethylpiperazine(2.2 g) were reacted in the same method as described in Preparation 9 to give the yellow above-indicated compound(1.5 g).

m.p.: 232°–234° C.(dec.)

Yield: 60%

NMR: δ(DMSO-d$_6$) 1.20(t,3H), 1.40(m,2H), 2.75–3.40 (m,6H), 3.60(m,4H), 7.40(d,1H), 8.40(d,1H), 8.85(s,1H)

Preparation 18:

Preparation of 1-cyclopropyl-6-fluoro-7-(2-methylpiperazinyl)-1,4-dihydro-4-thioquinoline-3-carboxylic acid 1-Cyclopropyl-6,7-difluoro-1,4-thioquinoline-3-carboxylic acid(2 g) and 2-methylpiperazine(2.2 g) were reacted in the same method as described in Preparation 9 to give the yellow above-indicated compound(1.3 g).

m.p.: 240°–242° C.(dec.)

Yield: 45%

NMR: δ(DMSO-d$_6$) 1.20–1.45(m,4H), 1.70(s,3H), 2.75–3.30(m,4H), 3.45–3.75(m,4H), 7.40(d,1H), 8.45(d, 1H), 8.80(s,1H)

Preparation 19:

Preparation of 1-ethyl-6-fluoro-7-piperazinyl-1,4-dihydro-4-thioquinoline

1-Ethyl-6,7-difluoro-1,4-thioquinoline(1 g) and piperazine(1.15 g) were reacted in the same method as described in Preparation 9 to give the yellow above-indicated compound(1.2 g).

m.p.: 106°–108° C.

Yield: 89%

NMR: δ(DMSO-d$_6$) 1.40(t,3H), 2.60–3.45(m,8H), 4.40 (q,2H), 7.05–7.85(m,3H), 8.40(d,1H)

Preparation 20:

Preparation or 1-ethyl-6-fluoro-7-(N-methylpiperazinyl)-1,4-dihydro-4-thioquinoline 1-Ethyl-6,7-difluoro-1,4-thioquinoline(1 g) and N-methylpiperazine (1.33 g) were reacted in the same method as described in Preparation 9 to give the yellow above-indicated compound(1.1 g).

m.p.: 184°–186° C.(dec.)

Yield: 77%

NMR: δ(DMSO-d$_6$) 1.40(t,3H), 2.28(s,3H),2.48–2.55(m, 4H), 3.25–3.35(m,4H), 4.42(q,2H), 7.05(d,1H), 7.15(d,1H), 7.88(d,1H), 8.40(d,1H)

Preparation 21:

Preparation of 1-ethyl-6-fluoro-7-(1-ethylpiperazinyl)-1,4-dihydro-4-thioquinoline 1-Ethyl-6,7-difluoro-1,4-thioquinoline(1 g) and 1-ethylpiperazine(1.52 g) were reacted in the same method as described in Preparation 9 to give the yellow above-indicated compound(1.23 g).

m.p.: 159°–161° C.

Yield: 82%

NMR: δ(DMSO-d$_6$) 1.20(t,3H), 1.40(t,3H), 2.40–3.50(m, 8H), 3.80(q,2H), 4.40(q,2H), 7.05–7.20(m,2H), 7.85(d,1H), 8.45(d,1H)

Preparation 22:

Preparation of 1-ethyl-6-fluoro-7-(2-methylpiperazinyl)-1,4-dihydro-4-thioquinoline 1-Ethyl-6,7-difluoro-1,4-thioquinoline(1 g) and 2-methylpiperazine(1.33 g) were reacted in the same method as described in Preparation 9 to give the yellow above-indicated compound(1.25 g).

m.p.: 125°–127° C.(dec.)

Yield: 87%

NMR: δ(DMSO-d$_6$) 1.15(d,3H), 1.40(t,3H), 2.40–3.60 (m,7H), 4.40(q,2H), 7.05–7.40(m,3H), 8.45(d,1H)

Preparation 23:

Preparation of 1-allyl-6-fluoro-7-piperazinyl-1,4-dihydro-4-thioquinoline

1-Allyl-6,7-difluoro-1,4-thioquinoline(2 g) and piperazine(2.2 g) were reacted in the same method as described in Preparation 9 to give the yellow above-indicated compound(2.3 g).

m.p.: 93°–95° C.

Yield: 86%

NMR: δ(DMSO-d$_6$) 2.64–3.40(m,8H), 5.10(d,2H), 5.15–6.20(m,3H), 7.05–7.90(m,3H), 8.40(d,1H)

Preparation 24:

Preparation of 1-allyl-6-fluoro-7-(N-methylpiperazinyl)-1,4-dihydro-4-thioquinoline 1-Allyl-6,7-difluoro-1,4-thioquinoline(2 g) and N-methylpiperazine(2.5 g) were reacted in the same method as described in Preparation 9 to give the yellow above-indicated compound(2.3 g).

m.p.: 145°–147° C.

Yield: 82%

NMR: δ(DMSO-d$_6$) 2.25(s,3H), 2.60–3.30(m,8H), 5.10 (d,2H), 5.30–6.05(m,3H), 7.10–7.80(m,3H), 8.40(d,1H)

Preparation 25:

Preparation of 1-allyl-6-fluoro-7-(1-ethylpiperazinyl)-1,4-dihydro-4-thioquinoline 1-Allyl-6,7-difluoro-1,4-thioquinoline(2 g) and 2-ethylpiperazine(2.9 g) were reacted in the same method as described in Preparation 9 to give the yellow above-indicated compound(2.35 g).

m.p.: 118°–120° C.

Yield: 80%

NMR: δ(DMSO-d$_6$) 1.15(t,3H), 2.30–3.30(m,10H), 5.05 (d,2H), 5.20–6.20(m,3H), 7.05–7.80(m,3H), 8.40(d,1H)

Preparation 26:

Preparation of 1-allyl-6-fluoro-7-(2-methylpiperazinyl)-1,4-dihydro-4-thioquinoline 1-Allyl-6,7-difluoro-1,4-thioquinoline(2 g) and 2-methylpiperazine(2.5 g) were reacted in the same method as described in Preparation 9 to give the yellow above-indicated compound(1.9 g).

m.p.: 162°–164° C.

Yield: 68%

NMR: δ(DMSO-d$_6$) 1.05(d,3H), 2.40–3.50(m,7H), 5.05 (d,2H), 5.20(d,1H),5.30(d,1H), 5.98–6.12(m,1H), 7.00(d,1H), 7.18(d,1H), 7.85 (d,1H), 8.38(d,1H)

EXAMPLE 1

Synthesis of 7-[(Z)-2-(2-aminothiazol-4-yl)-2-(methoxyimino)acetamide]-3-(1-methyl-6-fluoro-7-piperazinylquinolinium-4-yl)thiomethyl-3-cephem-4-carboxylate To a solution of 3-acetoxymethyl-7-[(Z)-2-(2-aminothiazol-4-yl)-2-(methoxyimino) acetamido]-3-cephem-4-carboxylic acid(0.73 g) suspended in 1:1(V/V) mixture of acetonitrile/water(30 ml) were added 1-methyl-6-fluoro-7-piperazinyl-1,4-dihydro-4-thioquinoline(0.5 g) and sodium iodide(2.4 g). The reaction mixture was heated to 60° C. for 5 hours.

The organic solvent was removed under reduced pressure. The residue was added acetone. The precipitates were filtered, and dried to give the above-indicated compound(0.6 g).

IR: (KBr, cm$^{-1}$) 1762(β-lactam)

NMR: δ(DMSO-d$_6$) 3.00–3.70(m,10H), 3.85(s,3H), 3.90 (s,3H), 4.30(s,2H), 5.05(d,1H), 5.65(dd,1H), 6.75(s,1H), 6.90–7.50(m,4H), 7.75(d,1H), 8.30(d,1H), 9.20–9.60(m,1H)

EXAMPLE 2

Synthesis of 7-[(Z)-2-(2-aminothiazol-4-yl)-2-(methoxyimino)acetamido]-3-[1-methyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.7 g) and 1-methyl-6-fluoro-7-(N-methylpiperazinyl)-1,4-dihydro-4-thioquinoline(0.5 g) were reacted in the same manner as described in Example 1 to give the above-indicated compound(0.61 g).

IR: (KBr, cm$^{-1}$) 1760(β-lactam)

NMR: δ(DMSO-d$_6$) 2.38(s,3H), 3.20–3.70(m,10H), 3.80 (s,3H), 3.90(s,3H), 4.25(s,2H), 4.95(d,1H), 5.50(dd,1H), 6.60(s,1H),6.80–7.40(m,4H),7.70(d,1H), 8.70(d,1H), 9.40–9.65(m,1H)

EXAMPLE 3

Synthesis of 7-[(Z)-2-(2-aminothiazol-4-yl)-2-(methoxyimino)acetamido]-3-[1-methyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.67 g) and 1-methyl-6-fluoro-7-(1-ethylpiperazinyl)-1,4-dihydro-4-thioquinoline(0.5 g) were reacted in the same manner as described in Example 1 to give the above-indicated compound(0.53 g).

IR: (KBr, cm$^{-1}$) 1760(β-lactam)

NMR: δ(DMSO-d$_6$) 1.00(t,3H), 2.40(q,2H), 2.80–3.70 (m,10H), 3.80(s,3H), 3.95(s,3H), 4.30(s,2H), 4.95(d,1H), 5.50(dd,1H), 6.65(s,1H), 6.80–7.30(m,4H), 7.90(d,1H), 8.40(d,1H), 9.30(d,1H)

EXAMPLE 4

Synthesis of 7-[(Z)-2-(2-aminothiazol-4-yl)-2-(methoxyimino)acetamido]-3-(1-methyl-6-fluoro-7-(2-methyl)piperazinylquinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.7 g) and 1-methyl-6-fluoro-7-(2-methylpiperazinyl)-1,4-dihydro-4-thioquinoline(0.5 g) were reacted in the same manner as described in Example 1 to give the above-indicated compound(0.57 g).

IR: (KBr, cm$^{-1}$) 1760(β-lactam)

NMR: δ(DMSO-$_6$) 1.70(s,3H), 2.75–3.70(m,9H), 3.70(s,3H), 3.85(s,3H), 4.40(s,2H), 5.00(d,1H), 5.50(dd,1H), 6.60 (s,1H), 6.90–7.30(m,4H), 7.80(d,1H), 9.40(d,1H)

EXAMPLE 5

Synthesis of 7-[(Z)-2-(2-aminothiazol-4-yl)-2-(methoxyimino)acetamido]-3-(1-cyclopropyl-6-fluoro-7-piperazinylquinolinium-4-yl)thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.68 g) and 1-cyclopropyl-6-fluoro-7-piperazinyl-1,4-dihydro-4-thioquinoline(0.5 g) were reacted in the same manner as described in Example 1 to give the above-indicated compound(0.53 g).

IR: (KBr,cm$^{-1}$) 1760(β-lactam)

NMR: δ(DMSO-d$_6$) 0.95–1.40(m,4H), 2.95–3.60(m,1H), 3.85(s,3H), 4.20(s.e.,2H), 4.95(d,1H), 5.50(dd,1H), 6.60–7.30(m,5H), 7.70(d,1H), 8.20(d,1H), 9.30–9.50(m,1H),

EXAMPLE 6

Synthesis of 7-[(Z)-2-(2-aminothiazol-4-yl)-2-(methoxyimino)acetamido]-3-[1-cyclopropyl-6-fluoro-7-(N-methylpiperazinyl)quinolinium-4-yl]thiomethyl-3-cephem-4-carboxylate 3-acetoxymethyl-7-[(Z) -2-(2-aminothiazol-4-yl)-2-(methoxyimino)acetamido]-3-cephem-4-carboxylic acid (0.65 g) and 1-cyclopropyl-6-fluoro-7-(N-methylpiperazinyl)-1,4-dihydro-4-thioquinoline(0.5 g) were reacted in the same manner as described in Example 1 to give the above-indicated compound(0.52 g).

IR: (KBr,cm$^{-1}$) 1760(β-lactam)

NMR: δ(DMSO-d$_6$) 1.00–1.45(m,4H), 2.30(s,3H), 3.10–3.80(m,11H), 3.90(s,3H), 4.00–4.40(s.e.,2H), 4.95(d, 1H), 5.50(dd,1H), 6.70(s,1H), 6.95–7.30(m,4H), 7.70(d, 1H), 8.45(d,1H), 9.42(d,1H)

EXAMPLE 7

Synthesis of 7-[(Z)-2-(2-aminothiazol-4-yl)-2-(methoxyimino)acetamido]-3-3-[1-cyclopropyl-6-fluoro-7-(1-ethylpiperazinyl)quinolinium-4-yl]-thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.63 g) and 1-cyclopropyl-6-fluoro-7-(1-ethylpiperazinyl)-1,4-dihydro-4-thioquinoline(0.5 g) were reacted in the same manner as described in Example 1 to give the above-indicated compound(0.57 g).

IR: (KBr, cm$^{-1}$) 1760(β-lactam)

NMR: δ(DMSO-d$_6$) 1.00–1.40(m,7H), 2.45(q,2H), 3.00–3.80(m,11H), 3.90(s,3H), 4.40(s,2H), 4.95(d,1H), 5.45 (dd,1H), 6.65(s,1H), 6.90–7.35(m,4H), 7.70(d,1H), 8.45(s, 1H), 9.40 (d,1H)

EXAMPLE 8

Synthesis of 7-[(Z)-2-(2-aminothiazol-4-yl)-2-(methoxyimino)acetamido]-3-[1-cyclopropyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.65 g) and 1-cyclopropyl-6-fluoro-7-(2-methylpiperazinyl)-1,4-dihydro-4-thioquinoline(0.5 g) were reacted in the same manner as described in Example 1 to give the above-indicated compound(0.61 g).

IR: (KBr,cm$^{-1}$) 1760(β-lactam)

NMR: δ(DMSO-d$_6$) 1.00–1.35(m,4H), 1.74(s,3H), 2.70–3.75(m,10H), 3.90(s,3H), 4.40(s,2H), 5.00(d,1H), 5.50 (dd,1H), 6.65(s,1H), 6.90–7.30(m,4H), 7.70(d,1H), 8.40(d, 1H), 9.40(d,1H)

EXAMPLE 9

Synthesis of 7-[(Z)-2-(2-aminothiazol-4-yl)-2-(methoxyimino)acetamido]-3-(1-ethyl-6-fluoro-7-piperazinylquinolinum-4-yl)thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-ethyl-6-fluoro-7-piperazinyl-1,4-dihydro-4-thioquinoine(0.21 g) were reacted in the same manner as described in Example 1 to give the above-indicated compound(0.24 g).

IR: (KBr,cm$^{-1}$) 1760(β-lactam)

NMR: δ(DMSO-d$_6$) 1.45(t,3H), 2.65–3.60(m,10H), 3.90 (s,3H), 4.10(q,2H), 4.40(s,2H), 5.00(d,1H), 5.50(dd,1H), 6.60(s,1H), 6.85–7.20(m,4H), 7.75(d,1H), 8.40(d,1H), 9.45 (d,1H)

EXAMPLE 10

Synthesis of 7-[(Z)-2-(2-aminothiazol-4-yl)-2-(methoxyimino)acetamido]-3-(1-ethyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-ethyl-6-fluoro-7-(N-methylpiperazinyl)-1,4-dihydro-4-thioquinoline(0.22 g) were reacted in the same manner as described in Example 1 to give the above-indicated compound(0.25 g).

IR: (KBr,cm$^{-1}$) 1760(β-lactam)

NMR: δ(DMSO-d$_6$) 1.40(t,3H), 2.45(s,3H), 2.65(t,4H), 3.30–3.60(m,6H), 3.90(s,3H), 4.10(q,2H), 4.40(s,2H), 5.05 (d,1H), 5.50(dd,1H), 6.65(s,1H), 7.05–7.40(m,4H), 7.45(d, 1H), 8.45(d,1H), 9.40(d,1H)

EXAMPLE 11

Synthesis of 7-[(Z)-2-(2-aminothiazol-4-yl)-2-(methoxyimino)acetamido]-3-[1-ethyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-ethyl-6-fluoro-7-(1-ethylpiperazinyl)-1,4-dihydro-4-thioquinoline(0.23 g) were reacted in the same manner as described in Example 1 to give the above-indicated compound(0.26 g).

IR: (KBr,cm$^{-1}$) 1760(β-lactam).

NMR: δ(DMSO-d$_6$) 1.20(t,3H), 1.40(t,3H), 2.30–2.85(m, 6H), 3.30–3.85 (m,6H), 3.85(s,3H), 4.10(q,2H), 4.40(s,2H), 4.95(d,1H), 5.50(dd,1H), 6.65(s,1H), 6.80–7.15(m,4H), 7.25(d,1H), 8.45(d,1H), 9.40(d,1H)

EXAMPLE 12

Synthesis of 7-[(Z)-2-(2-aminothiazol-4-yl)-2-(methoxyimino)acetamido]-3-[1-ethyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-ethyl-6-fluoro-7-(2-methylpiperazinyl)-1,4-dihydro-4-thioquinoline(0.22 g) were reacted in the same manner as described in Example 1 to give the above-indicated compound(0.26 g).

IR: (KBr,cm$^{-1}$) 1760(β-lactam)

NMR: δ(DMSO-d$_6$) 1.40(t,3H), 1.70(s,3H), 2.65–3.25(m, 3H), 3.45–3.75(m,6H), 3.90(s,3H), 4.10(q,2H), 4.45(s,2H), 5.00(d,1H), 5.50(dd,1H), 6.65(s,1H), 6.70–7.30(m,4H), 7.40(d,1H), 8.45(d,1H), 9.40(d,1H)

EXAMPLE 13

Synthesis of 7-[(Z)-2-(2-aminothiazol-4-yl)-2-(methoxyimino)acetamido]-3-(1-allyl-6-fluoro-7-piperazinylquinolinium-4-yl)thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-allyl-6-fluoro-7-piperazinyl-1,4-dihydro-4-thioquinoline(0.2 g) were reacted in the same manner as described in Example 1 to give the above-indicated compound(0.23 g).

IR: (KBr,cm$^{-1}$) 1760(β-lactam)

NMR: δ(DMSO-d$_6$) 2.65–3.60 (m,10H), 3.90(s,3H), 4.40–4.50(m,4H), 4.95(d,1H), 5.20(d,2H), 5.45(dd,1H), 6.10–6.25(m,1H), 6.65 (s,1H), 6.90–7.45(m,4H), 7.75(d, 1H), 8.40(d,1H), 9.40(d,1H)

EXAMPLE 14

Synthesis of 7-[(Z)-2-(2-aminothiazol-4-yl)-2-(methoxyimino)acetamido]-3-[1-allyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-allyl-6-fluoro-7-(N-methylpiperazinyl)-1,4-dihydro-4-thioquinoline(0.2 g) were reacted in the same manner as described in Example 1 to give the above-indicated compound(0.25 g).

IR: (KBr,cm$^{-1}$) 1760(β-lactam)

NMR: δ(DMSO-d$_6$) 2.40(s,3H), 2.65–3.60(m,10H), 3.90(s,3H), 4.40–4.50(m,4H), 7.55(d,1H), 8.40(d,1H), 9.45(d,1H)

EXAMPLE 15

Synthesis of 7-[(Z)-2(2-aminothiazol-4-yl)-2-(methoxyimino)acetamido]-3-[1-allyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.3 g) and 1-allyl-6-fluoro-7-(1-ethylpiperazinyl)-1,4-dihydro-4-thioquinoline(0.22 g) were reacted in the same manner as described in Example 1 to give the above-indicated compound(0.24 g).

IR: (KBr,cm$^{-1}$) 1760(β-lactam)

NMR: δ(DMSO-d$_6$) 1.20(t,3H), 2.35–2.70(m,6H), 3.30–3.65(m,6H), 3.95(s,3H), 4.35–4.50(m,4H), 4.95–5.05(m,3H), 5.45(dd,1H), 5.95–6.05(m,1H), 6.65(s,1H), 6.70–7.25(m,4H), 7.30(d,1H), 8.40(d,1H), 9.40(d,1H)

EXAMPLE 16

Synthesis of 7-[(Z)-2-(2-aminothiazol-4-yl)-2-(methoxyimino)acetamido]-3-[1-allyl-6-fluoro-7-(2-methylpiperazinyl)quinolinium-4-yl]thiomethyl 3-cephem-4-carboxylate 3-acetoxymethyl-7-[(Z)-2-(2-aminothiazol-4-yl)-2-(methoxyimino)acetamido]-3-cephem-4-carboxylic acid (0.3g) and 1-allyl-6-fluoro-7-(2-methylpiperazinyl)-1,4-dihydro-4-thioquinoline(0.2 g) were reacted in the same manner as described in Example 1 to give the above-indicated compound(0.26 g).

IR: (KBr,cm$^{-1}$) 1760(β-lactam)

NMR: δ(DMSO-d$_6$) 1.70(s,3H), 2.70–3.20(m,3H), 3.45–3.70(m,6H), 3.90(s,3H) 4.40–4.50(m,4H), 5.00(d,1H), 5.10(d,2H), 5.45(dd,1H), 6.00–6.10(m,1H), 6.65(s,1H), 6.70–7.30(s,4H), 7.35(d,1H), 8.50(d,1H), 9.40(d,1H)

Example 17

Synthesis of 7-[(Z)-2-(2-aminothiazol-4-yl)-2-(methoxyimino)acetamido]-3-(1-methyl-6-fluoro-7-imidazolylquinolinium-4-yl)thiomethyl-3-cephem-4-carboxylate To a solution of 3-acetoxymethyl-7-[(Z)-2-(2-aminothiazol-4-yl)-2-(methoxyimino)acetamido]-3-cephem-4-carboxylic acid(0.8 g) suspended in 1:1(V/V) mixture of acetonitrile/water(40 ml) were added 1-methyl-6-fluoro-7-imidazolyl-1,4-dihydro-4-thioquinoine(0.51 g) and sodium iodide(2.6 g). The reaction mixture was heated to 60° C. for 5 hours. The organic solvent was removed under reduced pressure. The residue was added acetone. The precipitates were filtered, and chromatographed over silica gel. Elution with a 4:1(V/V) mixture of acetonitrile/water gave the above-indicated compound(0.65 g).

IR: (KBr,cm$^{-1}$) 1761(β-lactam)

NMR: δ(DMSO-d$_6$) 3.55(s,2H), 3.85(s,3H), 3.95(s,3H), 4.40(s,2H), 4.95(d,1H), 5.50(dd,1H), 6.65(s,1H), 6.70(d,1H), 6.80–7.40(m,6H), 7.85(s,1H), 8.50(d,1H), 9.40(d,1H)

EXAMPLE 18

Synthesis of 7-[(Z)-2-(2-aminothiazol-4-yl)-2-(methoxyimino)acetamido]-3-[1-methyl-6-fluoro-7-(4-methylimidazolyl)quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.45 g) and 1-methyl-6-fluoro-7-(4-methylimidazolyl)-1,4-dihydro-4-thioquinoline(0.3 g) were reacted in the same manner as described in Example 17 to give the above-indicated compound(0.38 g).

IR: (KBr,cm$^{-1}$) 1762(β-lactam)

NMR: δ(DMSO-d$_6$) 2.40(s,3H), 3.50(s,2H), 3.80(s,3H), 3.90(s,3H) 4.40(s,2H), 5.00(d,1H), 5.50(dd,1H), 6.60–6.85(m,3H), 7.05–7.60(m,5H), 8.50(d,1H), 9.40(d,1H)

EXAMPLE 19

Synthesis of 7-[(Z)-2-(2-aminothiazol-4-yl)-2-(methoxyimino)acetamide]-3-(1-cyclopropyl-6-fluoro-7-imidazolylquinolinium-4-yl)thiomethyl-3-cephem-4-carboxylate 3-acetoxymethyl-7-[(Z)-2-(2-aminothiazol-4-yl)-2-(methoxyimino)acetamide]-3-cephem-4-carboxylic acid(0.8 g) and 1-cyclopropyl-6-fluoro-7-imidazolyl-1,4-dihydro-4-thioquinoline(0.55 g) were reacted in the same manner as described in Example 17 to give the above-indicated compound(0.66 g).

IR: (KBr,cm$^{-1}$) 1762(β-lactam)

NMR: δ(DMSO-d$_6$) 0.95–1.40(m,4H), 3.40–3.65(m,3H), 3.90(s,3H), 4.40(s,2H), 4.95(d,1H), 5.50(dd,1H), 6.65(s,1H), 6.85–7.35(m,6H) 7.40(d,1H), 7.85(s,1H), 8.50(d,1H), 9.40(d,1H)

EXAMPLE 20

Synthesis of 7-[(Z)-2-(2-aminothiazol-4-yl)-2-(methoxyimino)acetamido]-3-[1-cyclopropyl-6-fluoro-7-(4-methylimidazolyl)quinolinium-4-yl] thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.8 g) and 1-cyclopropyl-6-fluoro-7-(4-methylimidazolyl)-1,4-dihydro-4-thioquinoline(0.58 g) were reacted in the same manner as described in Example 17 to give the above-indicated compound(0.67 g).

IR: (KBr,cm$^{-1}$) 1761(β-lactam)

NMR: δ(DMSO-d$_6$) 0.90–1.40(m,4H), 2.45(s,3H), 3.45–3.60(m,3H), 3.90(s,3H), 4.40(s,2H), 5.00(d,1H), 5.50(dd,1H), 6.65(s,1H), 6.90–7.50(m,6H), 7.65(s,1H), 8.45(d,1H), 9.40(d,1H)

EXAMPLE 21

Synthesis of 7-[(Z)-2-(2-aminothiazol-4-yl)-2-(allyloxyimino)acetamido]-3-(1-methyl-6-fluoro-7-piperazinylquinolinium-4-yl)thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.4 g) and 1-methyl-6-fluoro-7-piperazinyl-1,4-dihydro-4-thioquinoline(0.26 g) were reacted in the same manner as described in Example 1 to give the above-indicated compound(0.34 g).

IR: (KBr,cm$^{-1}$) 1762(β-lactam)

NMR: δ(DMSO-d$_6$) 2.65–3.10(m,8H), 3.58(s,2H), 3.90 (s,3H), 4.40(s,2H), 5.05–5.80(m,4H), 5.85–6.15(m,3H), 6.85(s,1H), 6.95–7.30(m,4H), 7.65(d,1H), 8.40(d,1H), 9.40 (d,1H),

EXAMPLE 22

Synthesis of 7-[(Z)-2-(2-aminothiazol-4-yl)-2-(allyloxyimino) acetamido]-3-[1-methyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.4 g) and 1-methyl-6-fluoro-7-(N-methylpiperazinyl)-1,4-dihydro-4-thioquinoline(0.27 g) were reacted in the same manner as described in Example 1 to give the above-indicated compound(0.33 g).

IR: (KBr,cm$^{-1}$) 1760(β-lactam)

NMR: δ(DMSO-d$_6$) 2.40(s,3H), 2.60–3.65(m,10H), 3.80 (s,3H), 4.40(s,2H), 5.00–6.10(m,7H), 6.55–7.05(m,4H), 8.40(d,1H), 9.45(d,1H)

EXAMPLE 23

Synthesis of 7-[(Z)-2-(2-aminothiazol-4-yl)-2-(allyloxyimino) acetamido]-3-[1-methyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.4 g) and 1-methyl-6-fluoro-7-(1-ethylpiperazinyl)-1,4-dihydro-4-thioquinoline(0.28 g) were reacted in the same manner as described in Example 1 to give the above-indicated compound(0.33 g).

IR: (KBr,cm$^{-1}$) 1761(β-lactam)

NMR: δ(DMSO-d$_6$) 1.20(t,3H), 2.35–2.80(m,6H), 3.30–3.60(m,6H), 3.80(s,3H), 4.45(s,2H), 5.05–5.90(m,6H), 6.10–6.70(m,3H), 7.05–7.25 (m,2H), 8.50(d,1H), 9.45(d, 1H),

EXAMPLE 24

Synthesis of 7-[(Z)-2-(2-aminothiazol-4-yl)-2-(allyloxyimino)acetamido]-3-[1-methyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.4 g) and 1-methyl-6-fluoro-7-(2-methylpiperazinyl)-1,4-dihydro-4-thioquinoline(0.27 g) were reacted in the same manner as described in Example 1 to give the above-indicated compound(0.34 g).

IR: (KBr,cm$^{-1}$) 1762(β-lactam)

NMR: δ(DMSO-d$_6$) 1.70(s,3H), 2.70–3.75(m,9H), 3.85 (s,3H), 4.45(s,2H), 5.00–5.80(m,6H), 5.95–6.65(m,3H), 7.05–7.30(m,2H), 8.50(d,1H), 9.40(d,1H)

EXAMPLE 25

Synthesis of 7-[(Z)-2-(2-aminothiazol-4-yl)-2-(allyloxyimino)acetamido]-3-(1-cyclopropyl-6-fluoro-7-piperazinylquinolinium-4-yl)thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.3 g) and 1-cyclopropyl-6-fluoro-7-piperazinyl-1,4-dihydro-4-thioquinoline(0.2 g) were reacted in the same manner as described in Example 1 to give the above-indicated compound(0.25 g).

IR: (KBr,cm$^{-1}$) 1760(β-lactam)

NMR: δ(DMSO-d$_6$) 0.85–1.40(m,4H), 2.80–3.90(m, 11H), 4.30–4.80(m,4H), 4.90–5.30(m,3H), 6.90–7.56(m, 5H), 7.70(d,1H), 8.20(d,1H), 9.20–9.50(m,1H)

EXAMPLE 26

Synthesis of 7-[(Z)-2-(2-aminothiazol-4-yl)-2-(allyloxyimino)acetamido]-3-[1-cyclopropyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.3 g) and 1-cyclopropyl-6-fluoro-7-(N-methylpiperazinyl)-1,4-dihydro-4-thioquinoline(0.22 g) were reacted in the same manner as described in Example 1 to give the above-indicated compound(0.34 g).

IR: (KBr,cm$^{-1}$) 1761(β-lactam)

NMR: δ(DMSO-d$_6$) 0.95–1.40(m,4H), 2.35(s,3H), 3.00–3.70(m,11H), 4.42–4.80(m,3H), 5.00–5.40(m,3H), 5.70–6.00(m,3H), 6.00(s,1H),6.95–7.40(m,4H),7.70(d,1H), 8.20(d,1H), 9.40(d,1H)

EXAMPLE 27

Synthesis of 7-[(Z)-2-(2-aminothiazol-4-yl)-2-(allyloxyimino)acetamido]-3-[1-cyclopropyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.3 g) and 1-cyclopropyl-6-fluoro-7-(1-ethylpiperazinyl)- 1,4-dihydro-4-thioquinoline(0.23 g) were reacted in the same manner as described in Example 1 to give the above-indicated compound(0.24 g).

IR: (KBr,cm$^{-1}$) 1761(β-lactam)

NMR: δ(DMSO-d$_6$) 0.90–1.40(m,7H), 2.45–3.55(m, 13H), 4.42–4.90(m,3H), 5.05–5.50(m,3H), 5.65–6.10(m, 3H),8.50(s,1H), 6.90–7.30(m,4H) 7.45(d,1H), 8.45(d,1H), 9.45(d,1H)

EXAMPLE 28

Synthesis of 7-[(Z)-2-(2-aminothiazol-4-yl)-2-(allyloxyimino)acetamido]-3-[1-cyclopropyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid(0.3 g) and 1-cyclopropyl-6-fluoro-7-(2-methylpiperazinyl)-4-dihydro-4-thioquinoline(0.22 g) were reacted in the same manner as described in Example 1 to give the above-indicated compound(0.23 g).

IR: (KBr,cm$^{-1}$) 1762(β-lactam)

NMR: δ(DMSO-d$_6$) 1.00–1.40(m,4H), 1.70(s,3H), 2.90–3.75(m,19H), 4.45–4.95(m,3H), 5.00–5.45(m,3H), 5.70–6.15(m,3H), 6.60(s,1H), 6.80–7.25(m,4H), 7.40(d, 1H), 8.50(d,1H), 9.45(d,1H)

EXAMPLE 29

Synthesis of 7-[(Z)-2-(2-aminothiazol-4-yl)-2-(allyloxyimino)acetamido]-3-(1-ethyl-6-fluoro-7-piperazinylquinolinium-4-yl)thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid (0.15 g) and 1-ethyl-6-fluoro-7-piperazinyl-1,4-dihydro-4-thioquinoline(0.1 g) were reacted in the same manner as described in Example 1 to give the above-indicated compound(0.11 g).

IR: (KBr,cm$^{-1}$) 1760(β-lactam)

NMR: δ(DMSO-d$_6$) 1.45(t,3H), 2.65–3.55(m,10H), 4.10 (q,2H), 4.45–5.40(m,6H), 5.75–6.20(m,3H), 6.60(s,1H), 6.90–7.55 (m,4H), 7.70(d,1H), 8.40(d,1H), 9.40(d,1H),

EXAMPLE 30

Synthesis of 7-[(Z)-2-(2-aminothiazol-4-yl)-2-(allyloxyimino)acetamido]-3-[1-ethyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid (0.15 g) and 1-ethyl-6-fluoro-7-(N-methylpiperazinyl)-1,4-dihydro-4-thioquinoline(0.1 g) were reacted in the same manner as described in Example 1 to give the above-indicated compound(0.11 g).

IR: (KBr,cm$^{-1}$) 1760(β-lactam)

NMR: δ(DMSO-d$_6$) 1.40(t,3H), 2.40(s,3H), 2.60–3.60(m, 10H), 4.10(q,2H), 4.40–5.55(m,6H), 5.80–6.25(m,3H), 6.65 (s,1H), 6.90–7.35(m,4H), 7.40(d,1H), 8.45(d,1H), 9.45(d, 1H),

EXAMPLE 31

Synthesis of 7-[(Z)-2-(2-aminothiazol-4-yl)-2-(allyloxyimino)acetamido]-3-[1-ethyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid (0.15 g) and 1-ethyl-6-fluoro-7-(1-ethylpiperazinyl)-1,4-dihydro-4-thioquinoline(0.11 g) were reacted in the same manner as described in Example 1 to give the above-indicated compound(0.12 g).

IR: (KBr,cm$^{-1}$) 1760(β-lactam)

NMR: δ(DMSO-d$_6$) 1.20(t,3H), 1.40(t,3H), 2.50–3.55(m, 12H), 4.10(q,2H), 4.40–4.85(m,3H), 4.95–5.50(m,3H), 5.80–6.15(m,3H), 6.60(s,1H),6.75–7.20(m,4H), 7.30(d,1H), 8.45(d,1H), 9.40(d,1H)

EXAMPLE 32

Synthesis of 7-[(Z)-2-(2-aminothiazol-4-yl)-2-(allyloxyimino)acetamido]-3-[1-ethyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid (0.15 g) and 1-ethyl-6-fluoro-7-(2-methylpiperazinyl)-1,4-dihydro-4-thioquinoline(0.1 g) were reacted in the same manner as described in Example 1 to give the above-indicated compound(0.12 g).

IR: (KBr,cm$^{-1}$) 1761(β-lactam)

NMR: δ(DMSO-d$_6$) 1.40(t,3H), 1.70(s,3H), 2.65–3.70(m, 9H), 4.10(q,2H), 4.45–4.90(m,3H), 5.00–5.65(m,3H), 5.90–6.20(m,3H), 6.60–6.70(m,2H), 6.90–7.25(m,3H), 7.40 (d,1H), 8.45(d,1H), 9.40(d,1H)

EXAMPLE 33

Synthesis of 7-[(Z)-2-(2-aminothiazol-4-yl)-2-(allyloxyimino)acetamido]-3-(1-allyl-6-fluoro-7-piperazinylquinolinium-4-yl)thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid (0.15 g) and 1-allyl-6-fluoro-7-piperazinyl-1,4-dihydro-4-thioquinoline(0.1 g) were reacted in the same manner as described in Example 1 to give the above-indicated compound(0.12 g).

IR: (KBr,cm$^{-1}$) 1760(β-lactam)

NMR: δ(DMSO-d$_6$) 2.65–3.65(m,10H), 4.40–4.50(m, 4H), 4.95–6.20(m,10H), 6.65(s,1H), 6.90–7.50(m,4H), 7.75 (d,1H), 8.40(d,1H), 9.45(d,1H)

EXAMPLE 34

Synthesis of 7-[(Z)-2-(2-aminothiazol-4-yl)-2-(allyloxyimino)acetamido]-3-[1-allyl-6-fluoro-7-(N-methylpiperazinyl)quinolinium-4-yl]thiomethyl-3-cephem-4-carboxylate 3-acetoxymethyl-7-[(Z) -2-(2-aminothiazol-4-yl)-2-(allyloxyimino)acetamido]-3-cephem-4-carboxylic acid (0.15 g) and 1-allyl-6-fluoro-7-(N-methylpiperazinyl)-1,4-dihydro-4-thioquinoline(0.1 g) were reacted in the same manner as described in Example 1 to give the above-indicated compound(0.11 g).

IR: (KBr,cm$^{-1}$) 1758(β-lactam)

NMR: δ(DMSO-d$_6$) 2.40(s,3H), 2.70–3.55(m,10H), 4.45–4.55(m,4H), 4.95–5.45(m,6H), 5.50–6.15(m,4H), 6.60 (s,1H), 6.85–7.50(m,4H), 7.55(d,1H), 8.40(d,1H), 9.40(d, 1H)

EXAMPLE 35

Synthesis of 7-[(Z)-2-(2-aminothiazol-4-yl)-2-(allyloxyimino)acetamido]-3-[1-allyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(allyloxyimino)acetamido]-3-cephem-4-carboxylic acid (0.15 g) and 1-allyl-6-fluoro-7-(1-ethylpiperazinyl)-1,4-dihydro-4-thioquinoline(0.11 g) were reacted in the same manner as described in Example 1 to give the above-indicated compound(0.12 g).

IR: (KBr,cm$^{-1}$) 1759(β-lactam)

NMR: δ(DMSO-d$_6$) 1.15(t,3H), 2.40–3.50(m,12H),4.40 (m,4H), 4.95–5.60(m,6H), 5.75–6.15(m,4H), 6.60–6.70(m, 2H), 6.90–7.15(m,3H), 7.30(d,1H), 8.40(d,1H), 9.40(d,1H),

EXAMPLE 36

Synthesis of 7-[(Z)-2-(2-aminothiazol-4-yl)-2-(allyloxyimino)acetamido]-3-[1-allyl-6-fluoro-7-(2-methylpiperazinyl)quinolinium-4-yl]thiomethyl-3-cephem4-carboxylate 3-acetoxymethyl-7-[(Z)-2-(2-aminothiazol-4-yl)-2-(allyloxyimino)acetamido]-3-cephem-4-carboxylic acid (0.15 g) and 1-allyl-6-fluoro-7-(2-methylpiperazinyl)-1,4-dihydro-4-thioquinoline(0.1 g) were reacted in the same manner as described in Example 1 to give the above-indicated compound(0.11 g).

IR: (KBr,cm$^{-1}$) 1758(β-lactam)

NMR: δ(DMSO-d$_6$) 1.70(s,3H), 2.70–3.75 (m,9H), 4.45 (m,4H) 4.80–5.45(m,6H), 5.70–6.15(m,4H), 6.65(m,2H), 6.85–7.30(m,3H), 7.35(d,1H), 8.50(d,1H), 9.45(d,1H)

EXAMPLE 37

Synthesis of 7-[(Z)-2-(2-aminothiazol-4-yl)-2-(propargyloxyimino)acetamido]-3-(1-methyl-6-fluoro-7-piperazinylquinolinium-4-yl)thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.4 g) and 1-methyl-6-fluoro-7-piperazinyl-1,4-dihydro-4-thioquinoline(0.26 g) were reacted in the same manner as described in Example 1 to give the above-indicated compound(0.33 g).

IR: (KBr,cm$^{-1}$) 1759($\beta$-lactam)

NMR: $\delta$(DMSO-d$_6$) 2.60–3.50(m,9H), 3.65(s,2H), 3.90 (s,3H), 4.45(s,2H), 4.75(s,2H), 5.05(d,1H), 5.55(dd,1H), 6.65(s,1H), 6.80·7.50(m,4H), 7.65(d,1H), 8.40(d,1H), 9.45 (d,1H)

EXAMPLE 38

Synthesis of 7-[(Z)-2-(2-aminothiazol-4-yl)-2-(propargyloxyimino) acetamido]-3-[1-methyl-6-fluoro-7-(N-methylpiperazinyl)quinolinium-4-yl] thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.4 g) and 1-methyl-6-fluoro-7-(N-methylpiperazinyl)-1,4-dihydro-4-thioquinoline(0.27 g) were reacted in the same manner as described in Example 1 to give the above-indicated compound(0.34 g).

IR: (KBr,cm$^{-1}$) 1760($\beta$-lactam)

NMR: $\delta$(DMSO-d$_6$) 1.70(s,3H), 2.70–3.75 (m,9H), 4.45 (m,4H), 4.80–5.45(m,6H), 5.70–6.15(m,4H), 6.65 (m,2H), 6.85–7.30(m,3H), 7.35(d,1H), 8.50(d,1H), 9.45(d,1H)

EXAMPLE 39

Synthesis of 7-[(Z)-2-(2-aminothiazol-4-yl)-2-(propargyloxyimino) acetamido]-3-[1-methyl-6-fluoro-7-(1-ethylpiperazinyl)quinolinium-4-yl]-thiomethyl-3-cephem-4-carboxylate 3-acetoxymethyl-7-[(Z)-2-(2-aminothiazol-4-yl)-2-(propargyloxyimino)acetamido]--3-cephem-4-carboxylic acid(0.4 g) and 1-methyl-6-fluoro-7-(1-ethylpiperazinyl)-1,4-dihydro-4-thioquinoline(0.29 g) were reacted in the same manner as described in Example 1 to give the above-indicated compound(0.36 g).

IR: (KBr,cm$^{-1}$) 1760($\beta$-lactam)

NMR: $\delta$(DMSO-d$_6$) 1.15(t,3H), 2.40–3.50(m,11H), 3.60 (s,2H), 3.80(s,3H), 4.40(s,2H), 4.80(s,2H), 5.05(d,1H), 5.50 (dd,1H), 6.60(m,2H), 6.75–7.20(m,3H), 7.25(d,1H), 8.50(d,1H), 9.45(d,1H)

EXAMPLE 40

Synthesis of 7-[(Z)-2-(2-aminothiazol-4-yl)-2-(propargyloxyimino) acetamido]-3-[1-methyl-6-fluoro-7-(2-methylpiperazinyl)quinolinium-4-yl] thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.4 g) and 1-methyl-6-fluoro-7-(2-methylpiperazinyl)-1,4-dihydro-4-thioquinoline(0.27 g) were reacted in the same manner as described in Example 1 to give the above-indicated compound(0.35 g).

IR: (KBr,cm$^{-1}$) 1759($\beta$-lactam)

NMR: (DMSO-d$_6$) 1.70(s,3H), 2.70–3.70(m,10H), 3.85 (s,3H), 4.45(s,2H), 4.80(s,2H), 5.00(d,1H), 5.50(dd,1H), 6.65(m,2H), 6.85–7.20(m,3H), 7.30(d,1H), 8.50(d,1H), 9.45 (d,1H)

EXAMPLE 41

Synthesis of 7-[(Z)-2-(2-aminothiazol-4-yl)-2-(propargyloxyimino) acetamido]-3-(1-cyclopropyl-6-fluoro-7-piperazinylquinolinium-4-yl)thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.4 g) and 1-cyclopropyl-6-fluoro-7-piperazinyl-1,4-dihydro-4-thioquinoline(0.28 g) were reacted in the same manner as described in Example 1 to give the above-indicated compound(0.33 g).

IR: (KBr,cm$^{-1}$) 1758($\beta$-lactam)

NMR: $\delta$(DMSO-d$_6$) 0.90–1.40(m,4H), 2.60–3.40(m, 10H), 3.60(s,2H), 4.45(s,2H), 4.75(s,2H), 5.05(d,1H), 5.55 (dd,1H), 6.60(s,1H), 6.80–7.40(m,4H), 7.70(d,1H), 8.40(d, 1H), 9.45(d,1H)

EXAMPLE 42

Synthesis of 7-[(Z)-2-(2-aminothiazol-4-yl)-2-(propargyloxyimino) acetamido]-3-[1-cyclopropyl-6-fluoro-7-(N-methylpiperazinyl)quinolinium-4-yl] thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.4 g) and 1-cyclopropyl-6-fluoro-7-(N-methylpiperazinyl)-1,4-dihydro-4-thioquinoline(0.29 g) were reacted in the same manner as described in Example 1 to give the above-indicated compound(0.32 g).

IR: (KBr,cm$^{-1}$) 1760($\beta$-lactam)

NMR: $\delta$(DMSO-d$_6$) 0.95–1.40(m,4H), 2.35(s,3H), 2.65–3.60(m,12H), 4.40(s,2H), 4.70(s,2H), 4.95(d,1H), 5.50 (dd,1H), 6.65 (s,1H), 6.85–7.30(m,4H), 7.40(d,1H), 8.40(d, 1H), 9.40(d,1H)

EXAMPLE 43

Synthesis of 7-[(Z)-2-(2-aminothiazol-4-yl)-2-(propargyloxyimino) acetamido]-3-cephem-4-carboxylate 3-acetoxymethyl-7-[(Z) -2-(2-aminothiazol-4-yl)-2-(propargyloxyimino) acetamido]-3-cephem-4-carboxylic acid(0.4 g) and 1-cyclopropyl-6-fluoro-7-(1-ethylpiperazinyl)-1,4-dihydro-4-thioquinoline(0.3 g) were reacted in the same manner as described in Example 1 to give the above-indicated compound(0.32 g).

IR: (KBr,cm$^{-1}$) 1759($\beta$-lactam)

NMR: $\delta$(DMSO-d$_6$) 0.90–1.40(m,7H), 2.30–3.60(m, 14H), 4.45(s,2H), 4.70(s,2H), 4.95 (d,1H), 5.55(dd,1H), 6.60(s,1H), 6.90–7.35(m,4H), 7.40(d,1H), 8.45(d,1H), 9.40 (d,1H)

EXAMPLE 44

Synthesis of 7-[(Z)-2-(2-aminothiazol-4-yl)-2-(propargyloxyimino) acetamido]-3-[1-cyclopropyl-6-fluoro-7-(2-methylpiperazinyl)quinolinium-4-yl] thiomethyl-3-cephem-4-carboxylate 3-acetoxymethyl-7- [(Z)-2-(2-aminothiazol-4-yl)-2-(propargyloxyimino)acetamido]-3-cephem-4-carboxylic acid(0.4 g) and 1-cyclopropyl-6-fluoro-7-(2-methylpiperazinyl)-1,4-dihydro-4-thioquinoline(0.29 g) were reacted in the same manner as described in Example 1 to give the above-indicated compound(0.33 g).

IR: (KBr,cm$^{-1}$) 1759($\beta$-lactam)

NMR: $\delta$(DMSO-d$_6$) 0.95–1.40(m,4H), 1.70(s,3H), 2.70–3.75(m,11H), 4.40(s,2H), 4.75(s,2H), 5.05(d,1H), 5.45 (dd,1H), 6.65(s,1H), 6.85–7.30(m,4H), 7.40(d,1H), 8.50(d, 1H), 9.45(d,1H)

EXAMPLE 45

Synthesis of 7-[(Z)-2-(2-aminothiazol-4-yl)-2-(propargyloxyimino) acetamido]-3-(1-ethyl-6-fluoro-7-piperazinylquinolinium-4-yl)thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-ethyl-6-fluoro-7-piperazinyl-1,4-dihydro-4-thioquinoline(0.33 g) were reacted in the same manner as described in Example 1 to give the above-indicated compound(0.40 g).

IR: (KBr,cm$^{-1}$) 1760($\beta$-lactam)

NMR: $\delta$(DMSO-d$_6$) 1.40(t,3H), 2.60–3.50(m,11H), 4.10–4.70(m,6H), 5.00(d,1H), 5.50(dd,1H), 6.65(s,1H), 6.90–7.50(m,4H), 7.70(d,1H), 8.40(d,1H), 9.40(d,1H)

EXAMPLE 46

Synthesis of 7-[(Z)-2-(2-aminothiazol-4-yl)-2-(propargyloxyimino)acetamido]-3-[1-ethyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-ethyl-6-fluoro-7-(N-methylpiperazinyl)-1,4-dihydro-4-thioquinoline(0.35 g) were reacted in the same manner as described in Example 1 to give the above-indicated compound(0.39 g).

IR: (KBr,cm$^{-1}$) 1760($\beta$-lactam)

NMR: $\delta$(DMSO-d$_6$) 1.40(t,3H), 2.40(s,3H), 2.65–3.55(m, 11H), 4.10–4.75(m,6H), 4.95(d,1H), 5.50(dd,1H), 6.65(s, 1H), 6.85–7.30(m,4H), 7.40(d,1H), 8.45(d,1H), 9.45(d,1H)

EXAMPLE 47

Synthesis of 7-[(Z)-2-(2-aminothiazol-4-yl)-2-(propargyloxyimino)acetamido]-3-[1-ethyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-ethyl-6-fluoro-7-(1-ethylpiperazinyl)-1,4-dihydro-4-thioquinoline(0.37 g) were reacted in the same manner as described in Example 1 to give the above-indicated compound(0.45 g).

IR: (KBr,cm$^{-1}$) 1760($\beta$-lactam)

NMR: $\delta$(DMSO-d$_6$) 1.20(t,3H), 1.40(t,3H), 2.30–3.60(m, 13H), 4.10–4.40(m,4H), 4.80(s,2H), 5.00(d,1H), 5.45(dd, 1H), 6.70(m,2H), 6.85–7.20(m,3H), 7.25(d,1H), 8.45(d,1H), 9.45(d,1H)

EXAMPLE 48

Synthesis of 7-[(Z)-2-(2-aminothiazol-4-yl)-2-(propargyloxyimino) acetamido]-3-[1-ethyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-ethyl-6-fluoro-7-(2-methylpiperazinyl)-1,4-dihydro-4-thioquinoline(0.35 g) were reacted in the same manner as described in Example 1 to give the above-indicated compound(0.40 g).

IR: (KBr,cm$^{-1}$) 1760($\beta$-lactam)

NMR: $\delta$(DMSO-d$_6$) 1.40(t,3H), 1.70(s,3H), 2.65–3.70(m, 10H), 4.10–4.80(m,6H), 5.00(d,1H), 5.60(dd,1H), 6.65(m, 2H), 6.85–7.30(m,3H), 7.35(d,1H), 8.45(d,1H), 9.40(d,1H)

EXAMPLE 49

Synthesis of 7-[(Z)-2-(2-aminothiazol-4-yl)-2-(propargyloxyimino) acetamido]-3-(1-allyl -6-fluoro-7-piperazinylquinolinium-4-yl)thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-allyl-6-fluoro-7-piperazinyl-1,4-dihydro-4-thioquinoline(0.31 g) were reacted in the same manner as described in Example 1 to give the above-indicated compound(0.41 g).

IR: (KBr,cm$^{-1}$) 1758($\beta$-lactam)

NMR: $\delta$(DMSO-d$_6$) 2.65–3.60(m,11H), 4.40–4.80(m, 6H), 5.00–5.25(m,3H), 5.65(dd,1H), 6.05–6.20(m,1H), 6.65 (s,1H), 6.85–7.40(m,4H), 7.80(d,1H), 8.40(d,1H), 9.45(d, 1H)

EXAMPLE 50

Synthesis of 7-[(Z)-2-(2-aminothiazol-4-yl)-2-(propargyloxyimino)acetamido]-3-[1-allyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-allyl-6-fluoro-7-(N-methylpiperazinyl)-1,4-dihydro-4-thioquinoline(0.34 g) were reacted in the same manner as described in Example. 1 to give the above-indicated compound(0.42 g).

IR: (KBr,cm$^{-1}$) 1759($\beta$-lactam)

NMR: $\delta$(DMSO-d$_6$) 2.40(s,3H), 2.65–3.55(m,11H), 4.45–4.70(m,6H), 5.00(m,3H), 5.60(dd,1H), 5.90–6.05(m, 1H), 6.60(s,1H), 6.80–7.40(m,1H), 7.55(d,1H), 8.40(d,1H), 9.45(d,1H)

EXAMPLE 51

Synthesis of 7-[(Z)-2-(2-aminothiazol-4-yl)-2-(propargyloxyimino) acetamido]-3-[1-allyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-allyl-6-fluoro-7-(1-ethylpiperazinyl)-1,4-dihydro-4-thioquinoline(0.35 g) were reacted in the same manner as described in Example 1 to give the above-indicated compound(0.40 g).

IR: (KBr,cm$^{-1}$) 1760($\beta$-lactam)

NMR: $\delta$(DMSO-d$_6$) 1.20(t,3H), 2.30–3.55(m,13H), 4.40–4.80(m,6H), 4.95(m,3H), 5.60(dd,1H), 5.95–6.10(m, 1H), 6.65(m,2H), 6.80–7.20(m,3H), 7.30(d,1H), 8.40(d,1H), 9.45(d,1H)

EXAMPLE 52

Synthesis of 7-[(Z)-2-(2-aminothiazol-4-yl)-2-(propargyloxyimino) acetamido]-3-[1-allyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(propargyloxyimino)acetamido]-3-cephem-4-carboxylic acid(0.5 g) and 1-allyl-6-fluoro-7-(2-methylpiperazinyl)-1,4-dihydro-4-thioquinoline(0.34 g) were reacted in the same manner as described in Example 1 to give the above-indicated compound(0.38 g).

IR: (KBr,cm$^{-1}$) 1759($\beta$-lactam)

NMR: $\delta$(DMSO-d$_6$) 1.70(s,3H), 2.70–3.75(m,10H), 4.40–4.75(m,6H), 5.00(d,1H), 5.10(d,2H), 5.55(dd,1H), 6.60(m,1H), 6.60(m,2H), 6.80–7.25(m,3H), 7.40(d,1H), 8.50(d,1H), 9.45(d,1H)

EXAMPLE 53

Synthesis of 7-[(Z)-2-(2-aminothiazol-4-yl)-2-(2-carboxyprop-2-oxyimino)acetamido]-3-(1-ethyl-6-fluoro-7-piperazinylquinolinium-4-yl)thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4- carboxylic acid(0.4 g) and 1-methyl-6-fluoro-7-piperazinyl-1,4-dihydro-4-thioquinoline(0.24 g) were reacted in the same manner as described in Example 17 to give the above-indicated compound(0.29 g).

IR: (KBr,cm$^{-1}$) 1763(β-lactam)

NMR: δ(DMSO-d$_6$) 1.45(d,6H), 2.60–3.55(m,10H), 3.90 (s,3H), 4.40(s,2H), 5.00(d,1H), 5.65(dd,1H), 6.70(s,1H), 7.00–7.40(m,4H), 7.65(d,1H), 8.40(d,1H), 9.25(d,1H)

EXAMPLE 54

Synthesis of 7-[(Z)-2-(2-aminothiazol-4-yl)-2-(2-carboxyprop-2-oxyimino)acetamido]-3-[1-methyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.4 g) and 1-methyl-6-fluoro-7-(N-methylpiperazinyl)-1,4-dihydro-4-thioquinoline(0.25 g) were reacted in the same manner as described in Example 17 to give the above-indicated compound(0.29 g).

IR: (KBr,cm$^{-1}$) 1763(β-lactam)

NMR: δ(DMSO-d$_6$) 1.38(s,3H), 1.42(s,3H), 2.30(s,3H), 2.70–3.60(m,10H), 3.95(s,3H), 4.40(s,2H), 5.06(d,1H), 5.65 (dd,1H), 6.70(s,1H), 7.05(d,1H), 7.15(m,2H), 7.35(d,1H), 7.85(d,1H), 8.40(d,1H), 9.10(d,1H)

EXAMPLE 55

Synthesis of 7-[(Z)-2-(2-aminothiazol-4-yl)-2-(2-carboxyprop-2-oxyimino)acetamido]-3-[1-methyl-6-fluoro-7-(1-ethylpiperazinyl)quinolinium-4-yl]thiomethyl-3-cephem4-carboxylate 3-acetoxymethyl-7-[(Z)-2-(2-aminothiazol-4-yl)-2-(2-carboxyprop-2-oxyimino)acetamido]-3-cephem-4-carboxylic acid(0.4 g) and 1-methyl-6-fluoro-7-(1-ethylpiperazinyl)-1,4-dihydro-4-thioquinoline(0.26 g) were reacted in the same manner as described in Example 17 to give the above-indicated compound(0.31 g).

IR: (KBr,cm$^{-1}$) 1761 (β-lactam)

NMR: δ(DMSO-d$_6$) 1.20(t,3H), 1.40(s,6H), 2.30–2.85(m, 6H), 3.20–3.55(m,6H), 3.95(s,3H), 4.40(s,2H), 5.10(d,1H), 5.65(dd,1H), 6.70(s,1H), 6.80(d,1H), 6.90–7.30(m,3H), 7.35(d,1H), 8.50(d,1H), 9.30(d,1H)

EXAMPLE 56

Synthesis of 7-[(Z)-2-(2-aminothiazol-4-yl)-2-(2-carboxyprop-2-oxyimino)acetamido]-3-[1-methyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.4 g) and 1-methyl-6-fluoro-7-(2-methylpiperazinyl)-1,4-dihydro-4-thioquinoline(0.25 g) were reacted in the same manner as described in Example 17 to give the above-indicated compound(0.30 g).

IR: (KBr,cm$^{-1}$) 1762(β-lactam)

NMR: δ(DMSO-d$_6$) 1.45(s,6H), 1.70(s,3H),2.70–3.70(m, 9H), 3.90(s,3H), 4.40(s,2H), 5.10(d,1H), 5.65(dd,1H), 6.70 (m,2H), 6.80–7.20(m,3H), 7.40(d,1H), 8.50(d,1H), 9.25(d, 1H)

EXAMPLE 57

Synthesis of 7-[(Z)-2-(2-aminothiazol-4-yl)-2-(2-carboxyprop-2-oxyimino)acetamido]-3-(1-cyclopropyl-6-fluoro-7-piperazinylquinolinium-4-yl)thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-cyclopropyl-6-fluoro-7-piperazinyl-1,4-dihydro-4-thioquinoline(0.54 g) were reacted in the same manner as described in Example 17 to give the above-indicated compound(0.67 g).

IR: (KBr,cm$^{-1}$) 1763(β-lactam)

NMR: δ(DMSO-d$_6$) 0.90–1.45(m,10H), 2.70–3.55 (m,11H), 4.40(s,2H), 5.05(d,1H), 5.65(dd,1H), 6.70(s,1H), 6.90–7.50(m,4H), 7.70(d,1H), 8.40(d,1H), 9.30(d,1H)

EXAMPLE 58

Synthesis of 7-[(Z)-2-(2-aminothiazol-4-yl)-2-(2-carboxyprop-2-oxyimino)acetamido]-3-[1-cyclopropyl-6-fluoro-7-(N-methylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-cyclopropyl-6-fluoro-7-(N-methylpiperazinyl)-1,4-dihydro-4-thioquinoline(0.56 g) were reacted in the same manner as described in Example 17 to give the above-indicated compound(0.66 g).

IR: (KBr,cm$^{-1}$) 1763(β-lactam)

NMR: δ(DMSO-d$_6$) 0.95–1.50(m,10H), 2.40(s,3H), 2.60–3.55(m,11H), 4.40(s,2H), 5.10(d,1H), 5.65(dd,1H), 6.70(s,1H), 6.85–7.30(m,4H), 7.40(d,1H), 8.40(d,1H), 9.20 (d,1H)

EXAMPLE 59

Synthesis of 7-[(Z)-2-(2-aminothiazol-4-yl)-2-(2-carboxyprop-2-oxyimino)acetamido]-3-[1-cyclopropyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-cyclopropyl-6-fluoro-7-(1-ethylpiperazinyl)-1,4-dihydro-4-thioquinoline(0.58 g) were reacted in the same manner as described in Example 17 to give the above-indicated compound(0.68 g).

IR: (KBr, cm$^{-1}$) 1762(β-lactam)

NMR: δ(DMSO-d$_6$) 1.00–1.50(m,13H), 2.40–2.65(m, 6H), 3.30–3.60(m,7H), 4.25(s.e., 2H), 5.00(d,1H), 5.65(dd, 1H), 6.70(s,1H), 7.10(d,1H), 7.50(d,1H), 7.75(d,1H), 7.85 (d,1H), 8.10(d,1H), 8.35(d,1H), 8.90(d,1H)

EXAMPLE 60

Synthesis of 7-[(Z)-2-(2-aminothiazol-4-yl)-2-(2-carboxyprop-2-oxyimino)acetamido]-3-[1-cyclopropyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-cyclopropyl-6-fluoro-7-(2-methylpiperazinyl)-1,4-dihydro-4-thioquinoline(0.56 g) were reacted in the same manner as described in Example 17 to give the above-indicated compound(0.64 g).

IR: (KBr,cm$^{-1}$) 1762(β-lactam)

NMR: δ(DMSO-d$_6$) 1.00–1.45(m,10H), 1.70(s,3H), 2.70–3.70(m,10H), 4.25(s,2H), 5.00(d,1H), 5.60(dd,1H), 6.70(s,1H), 6.85–7.30(m,4H), 7.50(d,1H), 8.50(d,1H), 9.20 (d,1H)

EXAMPLE 61

Synthesis of 7-[(Z)-2-(2-aminothiazol-4-yl)-2-(2-carboxyprop-2-oxyimino)acetamido]- 3-[1-ethyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4yl)-2-(2-carboxyprop-2-oxyimino)acetamido]-3-cephem-4-carboxylic acid(0.8 g) and 1-ethyl-6-fluoro-7-(1-ethylpiperazinyl)-1,4-dihydro-4-thioquinoline(0.53 g) were reacted in the same manner as described in Example 17 to give the above-indicated compound(0.67 g).

IR: (KBr,cm$^{-1}$) 1763($\beta$-lactam)

NMR: $\delta$(DMSO-d$_6$) 1.20(t,3H), 1.40(t,3H), 1.45(s,6H), 2.50–3.55(m,12H), 4.10–4.45(m,4H), 5.00(d,1H), 5.65(dd, 1H), 6.70(s,1H), 6.80–7.20(m,4H), 7.40(d,1H), 8.45(d,1H), 9.20(d,1H)

EXAMPLE 62

Synthesis of 7-[(Z)-2-(2-aminothiazol-4-yl)-2-(2-carboxyprop-2-oxyimino)acetamido]-3-[1-ethyl-6-fluoro-7-(2-methylpiperazinyl)quinolinium-4-yl]thiomethyl]-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-ethyl-6-fluoro-7-(2-methylpiperazinyl)-1,4-dihydro-4-thioquinoline(0.51 g) were reacted in the same manner as described in Example 17 to give the above-indicated compound(0.65 g).

IR: (KBr,cm$^{-1}$) 1762($\beta$-lactam)

NMR: $\delta$(DMSO-d$_6$) 1.40(t,3H), 1.45(s,6H), 1.70(s,3H), 2.65–3.50(m,9H) 4.15–4.35(m,4H), 5.00(d,1H), 5.65(dd, 1H), 6.70(m,2H), 6.85–7.30(m,3H), 7.50(d,1H), 8.45(d,1H), 9.30(d,1H)

EXAMPLE 63

Synthesis of 7-[(Z)-2-(2-aminothiazol-4-yl)-2-(2-carboxyprop-2-oxyimino)acetamido]-3-[1-allyl-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-allyl-6-fluoro-7-(1-ethylpiperazinyl)-1,4-dihydro-4-thioquinoline(0.51 g) were reacted in the same manner as described in Example 17 to give the above-indicated compound(0.66 g).

IR: (KBr,cm$^{-1}$) 1763($\beta$-lactam)

NMR: $\delta$(DMSO-d$_6$) 1.20(t,3H), 1.40(s,6H), 2.50–3.50(m, 12H), 4.40–4.55(m,4H), 4.95–5.10(m,3H), 5.70–6.00(m, 2H), 6.70(m,2H), 6.80–7.30(m,3H), 7.55(d,1H), 8.40(d,1H), 9.25(d,1H)

EXAMPLE 64

Synthesis of 7-[(Z)-2-(2-aminothiazol-4-yl)-2-(2-carboxyprop-2-oxyimino)acetamido]-3-[1-allyl-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.8 g) and 1-allyl-6-fluoro-7-(2-methylpiperazinyl)- 1,4-dihydro-4-thioquinoline(0.49 g) were reacted in the same manner as described in Example 17 to give the above-indicated compound(0.63 g).

IR: (KBr,cm$^{-1}$) 1763($\beta$-lactam)

NMR: $\delta$(DMSO-d$_6$) 1.40(s,6H), 1.70(s,3H), 2.70–3.75 (m,9H), 4.45(m,4H), 5.00–5.10(m,3H), 5.65(dd,1H), 6.05 (m,1), 6.65(m,2H), 6.90–7.30(m,3H), 7.45(d,1H), 8.50(d, 1H), 9.45(d,1H)

EXAMPLE 65

Synthesis of 7-[(Z)-2-(2-aminothiazol-4-yl)-2-(2-carboxyprop-2-oxyimino)acetamido]-3-(1-ethyl-6-fluoro-7-imidazolylquinolinium-4-yl)thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.4 g) and 1-methyl-6-fluoro-7-imidazolyl-1,4-dihydro-4-thioquinoline(0.22 g) were reacted in the same manner as described in Example 17 to give the above-indicated compound(0.31 g).

IR: (KBr,cm$^{-1}$) 1760($\beta$-lactam)

NMR: $\delta$(DMSO-d$_6$) 1.50(s,6H), 3.65(s,2H), 3.90(s,3H), 4.45(s,2H), 5.00(d,1H), 5.65(dd,1H), 6.65(d,1H), 6.70(s, 1H), 6.85–7.40(m,6H), 7.85(s,1H), 8.50(d,1H), 9.40(d,1H)

EXAMPLE 66

Synthesis of 7-[(Z)-2-(2-aminothiazol-4-yl)-2-(2-carboxyprop-2-oxyimino)acetamido]-3-[1-methyl-6-fluoro-7-(4-methylimidazolyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.4 g) and 1-methyl-6-fluoro-7-(4-methylimidazolyl-1,4-dihydro-4-thioquinoline(0.23 g) were reacted in the same manner as described in Example 17 to give the above-indicated compound(0.33 g).

IR: (KBr,cm$^{-1}$) 1761($\beta$-lactam)

NMR: $\delta$(DMSO-d$_6$) 1.50(s,6H), 2.40(s,3H), 3.65(s,2H), 3.95(s,3H), 4.45(s,2H), 5.05(d,1H), 5.70(dd,1H), 6.60–6.85 (m,3H), 6.90–7.40(m,4H), 7.60(d,1H), 8.50(d,1H), 9.30(d, 1H)

EXAMPLE 67

Synthesis of 7-[(Z)-2-(2-aminothiazol-4-yl)-2-(2-carboxyprop-2-oxyimino)acetamido]-3-(1-cyclopropyl-6-fluoro-7-imidazolylquinolinium-4-yl) thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.3 g) and 1-cyclopropyl-6-fluoro-7-imidazolyl-1,4-dihydro-4-thioquinoline(0.18 g) were reacted in the same manner as described in Example 17 to give the above-indicated compound(0.24 g).

IR: (KBr,cm$^{-1}$) 1760($\beta$-lactam)

NMR: $\delta$(DMSO-d$_6$) 1.00–1.45(m,10H), 3.50–3.65(m, 3H), 4.45(s,2H), 5.10(d,1H), 5.70(dd,1H), 6.70(s,1H), 6.90–7.40(m,7H), 7.85(s,1H), 8.50(d,1H), 9.35(d,1H)

EXAMPLE 68

Synthesis of 7-[(Z)-2-(2-aminothiazol-4-yl)-2-(2-carboxyprop-2-oxyimino)acetamido]-3-[1-cyclopropyl-6-fluoro-7-(4-methylimidazolyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4- carboxylic acid(0.3 g) and 1-cyclopropyl-6-fluoro-7-(4-methylimidazolyl)-1,4-dihydro-4-thioquinoline(0.19 g) were reacted in the same manner as described in Example 17 to give the above-indicated compound(0.23 g).

IR: (KBr,cm$^{-1}$) 1761(β-lactam)

NMR: δ(DMSO-d$_6$) 0.95–1.45(m,10H), 2.45(s,3H), 3.45–3.60(m,3H), 4.50(s,2H), 5.10(d,1H), 5.70 (dd,1H), 6.70 (s,1H), 6.90 (s,1H), 6.95–7.60 (m,6H ), 8.45(d,1H), 9.30(d,1H)

EXAMPLE 69

Synthesis of 7-[(Z)-2-(2-aminothiazol-4-yl)-2-(methoxyimino)acetamido]-3-[1-cyclopropyl-3-carboxylicacid-6-fluoro-7-(1-ethylpiperazinyl) quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.7 g) and 1-cyclopropyl-6-fluoro-7-(1-ethylpiperazinyl)-1,4-dihydro-4-thioquinoline-3-carboxylic acid(0.63 g) were reacted in the same manner as described in Example 17 to give the above-indicated compound(0.59 g).

IR: (KBr,cm$^{-1}$) 1761(β-lactam)

NMR: δ(DMSO-d$_6$) 1.00–1.40(m,7H), 2.75–3.70(m, 13H), 3.90(s,3H), 4.40(s,2H), 5.00(d,1H), 5.50(dd,1H), 6.65 (s,1H), 7.40(d,1H), 8.40(d,1H), 8.85(s,1H), 9.50(d,1H)

EXAMPLE 70

Synthesis of 7-[(Z)-2-(2-aminothiazol-4-yl)-2-(methoxyimino)acetamido]-3-[1-cyclopropyl-1-3-carboxylicacid-6-fluoro-7-(2-methylpiperazinyl) quinolinium-4-yl]thiomethyl-3-cephem-4-carboxylate 3-acetoxymethyl-7-[(Z)-2-(2-aminothiazol-4-yl)-2-(methoxyimino)acetamido]-3-cephem-4-carboxylic acid (0.6 g) and 1-cyclopropyl-6-fluoro-7-(2-methylpiperazinyl)-1,4-dihydro-4-thioquinoline-3-carboxylic acid(0.52 g) were reacted in the same manner as described in Example 17 to give the above-indicated compound(0.52 g).

IR: (KBr,cm$^{-1}$) 1760(β-lactam)

NMR: δ(DMSO-d$_6$) 1.10–1.45(m,4H), 1.70(s,3H), 2.75–3.70(m,10H), 3.90(s,3H), 4.40(s,2H), 5.05(d,1H), 5.50 (dd,1H), 6.65(s,1H), 7.40(d,1H), 8.45(d,1H), 8.75(s,1H), 9.50(d,1H)

EXAMPLE 71

Synthesis of 7-[(Z)-2-(2-aminothiazol-4-yl)-2-(2-carboxyprop-2-oxyimino)acetamido]-3-[1-cyclopropyl-3-carboxylicacid-6-fluoro-7-(1-ethylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid (0.4 g) and 1-cyclopropyl-6-fluoro-7-(1-ethylpiperazinyl)- 1,4-dihydro-4-thioquinoline-4-carboxylic acid(0.31 g) were reacted in the same manner as described in Example 17 to give the above-indicated compound(0.34 g).

IR: (KBr,cm$^{-1}$) 1760(β-lactam)

NMR: δ(DMSO-d$_6$) 1.00–1.50(m,13H), 2.75–3.60(m, 13H), 4.50(s,2H), 5.10(d,1H), 5.70(dd,1H), 6.70(s,1H), 6.95–7.40(m,3H), 8.40(d,1H), 8.80(s,1H), 9.55(d,1H)

EXAMPLE 72

Synthesis of 7-[(Z)-2-(2-aminothiazol-4-yl)-2-(2-carboxyprop-2-oxyimino)acetamido]-3-[1-cyclopropyl-3-carboxylicacid-6-fluoro-7-(2-methylpiperazinyl)quinolinium-4-yl]thiomethyl-3-cephem-4-carboxylate 3-acetoxymethyl-7-[(Z)-2-(2-aminothiazol-4-yl)-2-(2-carboxyprop-2-oxyimino)acetamido]-3-cephem-4-carboxylic acid(0.4 g) and 1-cyclopropyl-6-fluoro-7-(2-methylpiperazinyl)-1,4-dihydro-4-thioquinoline-3-carboxylic acid(0.3 g) were reacted in the same manner as described Example 17 to give the above-indicated compound(0.32 g).

IR: (KBr,cm$^{-1}$) 1760(β-lactam)

NMR: δ(DMSO-d$_6$) 1.10–1.45(m,10H), 1.70(s,3H), 2.75–3.60(m,10H) 4.50(s,2H), 5.10(d,1H), 5.70(dd,1H), 6.70(s,1H), 6.90–7.35(m,3H), 8.50(d,1H), 8.85(s,1H), 9.50 (d,1H)

In order to illustrate the usefulness of the invented compounds, the minimal inhibitory concentrations-(MIC) thereof against standard strains were determined and compared with Cefotaxime, a known compound.

Also, the in vitro antibacterial activity was determined by a two-fold dilution method as described below:

That is, the two-fold serial dilutions of the compound were made and dispersed in Muller Hinton Broth medium. Standard test strain which had the $10^6$ CFU per ml was inoculated on the medium, and was incubated at 37° C. for 18 to 20 hours. The results of the MIC tests are shown in Table 3.

TABLE 3

Antibacterial Activity (MIC, μg/ml)

| | Strains | | | | | | |
|---|---|---|---|---|---|---|---|
| Compound No. | Bacillus subtilis ATCC 6633 | Staphylococcus aureus ATCC 65389 | Staphylococcus epidermidis ATCC 12228 | Streptococcus faecalis ATCC 10541 | Pseudomonas aeurginosa NCTC 10490 | Esherichia coli ATCC 25922 | Klebsiella pneumoniae ATCC 10031 |
| I-1 | 0.2 | 0.2 | 0.1 | 0.05 | 1.56 | 0.78 | 0.2 |
| I-2 | 0.39 | 1.56 | 0.78 | 0.39 | 3.13 | 12.5 | 0.39 |
| I-3 | 0.2 | 0.05 | 0.1 | 0.025 | 0.78 | 0.78 | 0.1 |
| I-4 | 0.1 | 0.1 | 0.2 | 0.05 | 0.78 | 0.78 | 0.1 |
| I-5 | 0.39 | 1.56 | 0.78 | 0.39 | 3.13 | 12.5 | 0.1 |
| I-6 | 0.39 | 0.39 | 0.39 | 0.2 | 1.56 | 12.5 | 0.1 |
| I-7 | 0.2 | 0.39 | 0.2 | 0.05 | 0.39 | 0.78 | 0.05 |
| I-8 | 0.2 | 0.39 | 0.2 | 0.2 | 0.39 | 0.78 | 0.05 |
| I-9 | 0.1 | 0.2 | 0.2 | 0.1 | 3.13 | 1.56 | 0.78 |
| I-10 | 0.39 | 0.39 | 1.56 | 1.56 | 6.25 | 12.5 | 0.78 |

TABLE 3-continued

| | Antibacterial Activity (MIC, μg/ml) | | | | | | |
|---|---|---|---|---|---|---|---|
| | Strains | | | | | | |
| Compound No. | Bacillus subtilis ATCC 6633 | Staphylococcus aureus ATCC 65389 | Staphylococcus epidermidis ATCC 12228 | Streptococcus faecalis ATCC 10541 | Pseudomonas aeurginosa NCTC 10490 | Esherichia coli ATCC 25922 | Klebsiella pneumoniae ATCC 10031 |
|---|---|---|---|---|---|---|---|
| I-11 | 0.1 | 0.1 | 0.2 | 0.05 | 1.56 | 1.56 | 0.39 |
| I-12 | 0.1 | 0.1 | 0.2 | 0.025 | 1.56 | 1.56 | 0.39 |
| I-13 | 0.39 | 1.56 | 1.56 | 0.78 | 1.56 | 3.13 | 0.78 |
| I-14 | 0.1 | 0.78 | 0.39 | 0.2 | 3.13 | 3.13 | 1.56 |
| I-15 | 0.1 | 0.2 | 0.78 | 0.39 | 1.56 | 1.56 | 0.39 |
| I-16 | 0.2 | 0.2 | 0.39 | 0.78 | 1.56 | 1.56 | 0.39 |
| I-18 | 0.1 | 0.2 | 0.2 | 0.2 | 1.56 | — | — |
| I-20 | 0.2 | 0.78 | 0.39 | 0.2 | 1.56 | 1.56 | 0.1 |
| I-21 | 0.39 | 0.2 | 0.1 | 0.025 | 6.25 | 3.13 | 0.1 |
| I-22 | 0.39 | 0.2 | 0.1 | 0.013 | 3.13 | 6.25 | 0.39 |
| I-23 | 0.2 | 0.1 | 0.1 | 0.2 | 1.56 | 1.56 | 0.2 |
| I-24 | 0.2 | 0.1 | 0.1 | 0.1 | 0.78 | 1.56 | 0.2 |
| I-25 | 0.2 | 0.78 | 0.78 | 0.2 | 0.39 | 6.25 | 0.39 |
| I-26 | 0.1 | 0.39 | 1.56 | 0.2 | 0.39 | 6.25 | 0.2 |
| I-27 | 0.2 | 0.2 | 0.2 | 0.2 | 0.78 | — | 0.39 |
| I-28 | 0.39 | 0.2 | 0.2 | 0.2 | 1.56 | — | 0.78 |
| I-29 | 0.39 | 0.78 | 0.78 | 0.39 | 3.13 | 1.56 | 0.39 |
| I-30 | 0.39 | 1.56 | 0.78 | 0.39 | 6.25 | 3.13 | 0.78 |
| I-31 | 0.2 | 0.39 | 0.78 | 0.39 | 0.78 | 0.78 | 0.39 |
| I-32 | 0.39 | 0.39 | 0.78 | 0.39 | 1.56 | 0.78 | 0.39 |
| I-33 | 0.78 | 0.78 | 1.56 | 0.39 | 3.13 | 3.13 | 1.56 |
| I-34 | 0.78 | 1.56 | 1.56 | 0.78 | 6.25 | 3.13 | 1.56 |
| I-35 | 0.39 | 0.78 | 0.78 | 0.39 | 0.78 | 1.56 | 0.78 |
| I-36 | 0.39 | 0.78 | 1.56 | 0.39 | 1.56 | 1.56 | 0.78 |
| I-37 | 0.2 | 0.39 | 0.78 | 0.2 | 0.2 | — | 0.78 |
| I-38 | 0.78 | 0.78 | 0.39 | 0.2 | 0.78 | — | 3.13 |
| I-39 | 0.2 | 0.39 | 0.2 | 0.2 | 0.2 | — | 0.78 |
| I-40 | 0.2 | 0.39 | 0.1 | 0.2 | 0.2 | — | 0.78 |
| I-41 | 0.2 | 0.78 | 0.78 | 0.39 | 3.13 | 3.13 | 6.25 |
| I-42 | 0.2 | 0.78 | 0.78 | 0.39 | 3.13 | 3.13 | 3.13 |
| I-43 | 0.1 | 0.1 | 0.1 | 0.05 | 0.78 | 1.56 | 0.78 |
| I-44 | 0.05 | 0.39 | 0.2 | 0.2 | 1.56 | 1.56 | 0.78 |
| I-45 | 0.1 | 0.2 | 0.78 | 0.39 | 1.56 | 3.13 | 0.78 |
| I-46 | 0.78 | 0.78 | 0.39 | 0.2 | 6.25 | 12.5 | 6.25 |
| I-47 | 0.2 | 0.2 | 0.78 | 0.1 | 1.56 | 6.25 | 1.56 |
| I-48 | 0.1 | 0.39 | 0.78 | 0.39 | 1.56 | 3.13 | 1.56 |
| I-49 | 0.39 | 1.56 | 1.56 | 0.78 | 1.56 | 1.56 | 1.56 |
| I-50 | 0.78 | 3.13 | 3.13 | 1.56 | 3.13 | 3.13 | 3.13 |
| I-51 | 0.78 | 3.13 | 1.56 | 1.56 | 1.56 | 0.78 | 0.78 |
| I-52 | 0.39 | 3.13 | 1.56 | 0.78 | 1.56 | 0.78 | 1.56 |
| I-53 | 0.39 | 3.13 | 1.56 | 0.39 | 1.56 | — | 1.56 |
| I-54 | 0.78 | 6.25 | 3.13 | 1.56 | 3.13 | 6.25 | 3.13 |
| I-55 | 0.2 | 1.56 | 0.78 | 0.2 | 0.39 | 0.78 | 0.39 |
| I-56 | 0.2 | 0.78 | 0.78 | 0.39 | 0.78 | 0.39 | 0.39 |
| I-57 | 0.78 | 6.25 | 6.25 | 1.56 | 0.78 | 0.78 | 0.39 |
| I-59 | 0.39 | 0.78 | 1.56 | 0.78 | 0.78 | 0.78 | 0.39 |
| I-61 | 3.13 | 1.56 | 1.56 | 0.39 | 1.56 | 3.13 | 3.13 |
| I-64 | 1.56 | 3.13 | 1.56 | 0.39 | 3.13 | 1.56 | 1.56 |
| I-65 | 0.39 | 1.56 | 1.56 | 0.39 | 1.56 | — | 1.56 |
| I-68 | 0.78 | 1.56 | 1.56 | 0.2 | 0.78 | 1.56 | 0.78 |
| CTX | 0.2 | 0.78 | 0.78 | 0.39 | 1.56 | 0.78 | 0.39 |

*CTX: Cefotaxime

We claim:

1. A cephalosporin compound of formula (I)

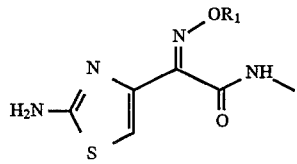

(I)

-continued

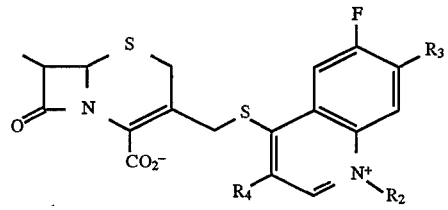

wherein $R_1$ is $C_{1-4}$ alkyl, $C_{3-4}$ alkenyl, $C_{3-4}$ alkynyl or —$C(R^a)(R^b)CO_2H$, wherein $R^a$ and $R^b$, same or different, are a hydrogen atom or a $C_{1-4}$ alkyl group;

$R_2$ is a $C_{1-4}$ alkyl, $C_{3-4}$ alkenyl, $C_{3-4}$ cycloalkyl or carboxyalkyl; $R_3$ is selected from unsubstituted piperazine, piperazine substituted with a $C_{1-4}$ alkyl at the N— or 2-position thereof, unsubstituted imidazole and imidazole substituted with $C_{1-4}$ alkyl;

$R_4$ is hydrogen or carboxylic acid; or a pharmaceutically acceptable salt thereof.

2. A process for preparing a cephalosporin compound of formula (I), or a pharmaceutically acceptable salt thereof, which comprises reacting a compound of formula (II) with a compound of formula (III) in the presence of a solvent;

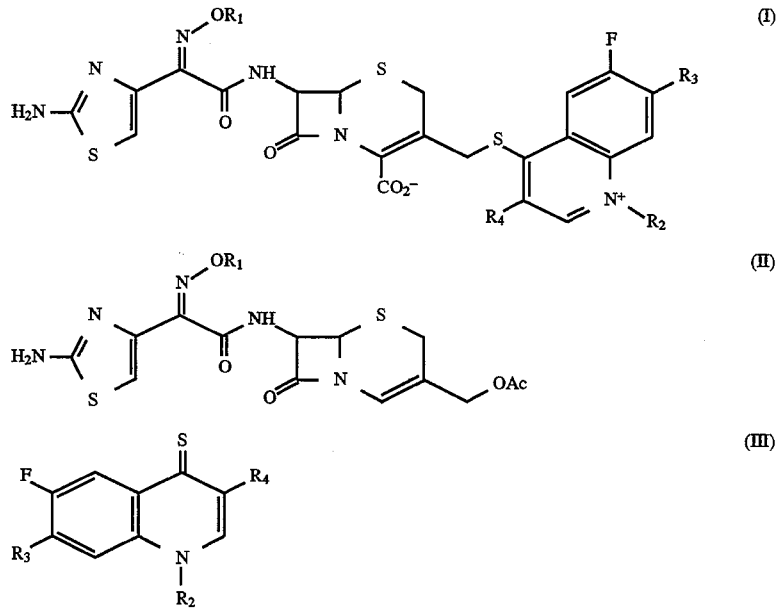

wherein $R_1$, $R_2$, $R_3$ and $R_4$ are the same as defined in claim 1.

3. A cephalosporin compound as recited in claim 1, wherein:

$R_1$ is selected from the group consisting of methyl, ethyl, allyl, propargyl, —$C(CH_3)_2CO_2H$ and —$CH_2CO_2H$;

$R_2$ is selected from the group consisting of methyl, ethyl, allyl, cyclopropyl and —$CH_2CO_2H$.

4. The process for preparing a cephalosporin compound as recited in claim 2, wherein:

$R_1$ is selected from the group consisting of methyl, ethyl, allyl, propargyl, —$C(CH_3)_2CO_2H$ and —$CH_2CO_2H$;

$R_2$ is selected from the group consisting of methyl, ethyl, allyl, cyclopropyl and —$CH_2CO_2H$;

$R_3$ is selected from unsubstituted piperazine, piperazine substituted with a $C_{1-4}$ alkyl at the N— or 2-position thereof, unsubstituted imidazole and imidazole substituted with $C_{1-4}$ alkyl.

* * * * *

UNITED STATES PATENT AND TRADEMARK OFFICE
CERTIFICATE OF CORRECTION

PATENT NO. : 5,663,331
DATED : September 2, 1997
INVENTOR(S) : Kee Won KIM et al.

It is certified that error appears in the above-identified patent and that said Letters Patent is hereby corrected as shown below:

On the title page:

Please amend the dates under [86] PCT No.: to read as follows:

Change "Jan. 24, 1995" to --Jan. 23, 1995--

Signed and Sealed this

Twenty-fourth Day of March, 1998

Attest:

BRUCE LEHMAN

Attesting Officer

*Commissioner of Patents and Trademarks*